US012654018B2

(12) United States Patent
Li et al.

(10) Patent No.: US 12,654,018 B2
(45) Date of Patent: *Jun. 16, 2026

(54) SYSTEMS, DEVICES, AND METHODS FOR IMPROVING PATIENT OUTCOMES IN IMPLANTABLE CARDIOVERTER DEFIBRILLATORS

(71) Applicant: North American EP Technology LLC, Edina, MN (US)

(72) Inventors: Yanhui Li, Edina, MN (US); Robert Joseph Gaskill, Edina, MN (US)

(73) Assignee: North American EP Technology LLC, Edina, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/214,400

(22) Filed: May 21, 2025

(65) Prior Publication Data

US 2025/0281757 A1     Sep. 11, 2025

Related U.S. Application Data

(63) Continuation of application No. 18/529,544, filed on Dec. 5, 2023, now Pat. No. 12,337,184.

(Continued)

(51) Int. Cl.
*A61N 1/365*     (2006.01)
*A61N 1/05*     (2006.01)
(Continued)

(52) U.S. Cl.
CPC ....... *A61N 1/36585* (2013.01); *A61N 1/0563* (2013.01); *A61N 1/3621* (2013.01); *A61N 1/39622* (2017.08)

(58) Field of Classification Search
CPC .............. A61N 1/36585; A61N 1/0563; A61N 1/3621; A61N 1/39622
See application file for complete search history.

(56) References Cited

U.S. PATENT DOCUMENTS 4,873,980 A     10/1989 Schaldach
5,374,282 A     12/1994 Nichols et al.
(Continued)

FOREIGN PATENT DOCUMENTS

WO     WO-2010088347 A1     8/2010
WO     WO-2024157153 A1     8/2024
(Continued)

OTHER PUBLICATIONS

[Author Unknown] "All pressure catheters are not created equal." Mikro-Cath™ Pressure Catheter; Millar, Inc. (2013); 2 pages. [Retrieved online] <URL: millar.com/mikro-cath>.
(Continued)

*Primary Examiner* — Brian T Gedeon
(74) *Attorney, Agent, or Firm* — COOLEY LLP

(57)     ABSTRACT

A method for improving treatment decisions of an implantable cardioverter defibrillator (ICD) implanted in a patient. The method includes determining an electrical status of a heart of the patient based on a first signal received from an electrical sensor of an ICD lead that is implanted in an anterior mediastinum of the patient. The electrical sensor is configured to detect electrical signals radiating from the heart. The method includes calculating a hemodynamic output of the heart based on a second signal received from a pressure sensor of the ICD lead. The pressure sensor is configured to detect pressure changes in the anterior mediastinum due to a mechanical functioning of the heart. The method includes defining a treatment decision based on a correlation between the electrical status and the hemodynamic output of the heart.

30 Claims, 5 Drawing Sheets

Related U.S. Application Data

(60) Provisional application No. 63/533,062, filed on Aug. 16, 2023.

(51) Int. Cl.
     *A61N 1/362*      (2006.01)
     *A61N 1/39*       (2006.01)

(56)               References Cited

U.S. PATENT DOCUMENTS

| | | | |
|---|---|---|---|
| 5,792,217 A | 8/1998 | Camps et al. |
| 5,871,512 A | 2/1999 | Hemming et al. |
| 5,899,927 A | 5/1999 | Ecker et al. |
| 7,181,276 B1 | 2/2007 | Province et al. |
| 8,613,744 B2 | 12/2013 | Pellegrino et al. |
| 9,002,467 B2 | 4/2015 | Smith et al. |
| 9,168,380 B1 | 10/2015 | Greenhut et al. |
| 9,242,113 B2 | 1/2016 | Smith et al. |
| 9,265,522 B2 | 2/2016 | Pellegrino et al. |
| 9,289,612 B1 | 3/2016 | Sambelashvili et al. |
| 9,320,886 B2 | 4/2016 | Rousso et al. |
| 9,352,164 B2 | 5/2016 | Smith et al. |
| 9,399,140 B2 | 7/2016 | Cho et al. |
| 9,492,668 B2 | 11/2016 | Sheldon et al. |
| 9,492,669 B2 | 11/2016 | Demmer et al. |
| 9,526,909 B2 | 12/2016 | Stahmann et al. |
| 9,561,053 B2 | 2/2017 | Bonde et al. |
| 9,592,391 B2 | 3/2017 | Stahmann et al. |
| 9,623,234 B2 | 4/2017 | Anderson |
| 9,669,230 B2 | 6/2017 | Koop |
| 9,694,189 B2 | 7/2017 | Maile et al. |
| 9,717,627 B2 | 8/2017 | Kuzma et al. |
| 9,724,519 B2 | 8/2017 | Demmer et al. |
| 9,757,570 B2 | 9/2017 | Maile et al. |
| 9,808,628 B2 | 11/2017 | Sheldon et al. |
| 9,808,631 B2 | 11/2017 | Maile et al. |
| 9,853,743 B2 | 12/2017 | Schmidt et al. |
| 9,956,390 B2 | 5/2018 | Rousso et al. |
| 9,956,414 B2 | 5/2018 | Kane et al. |
| 9,968,783 B2 | 5/2018 | Bullinga et al. |
| 9,968,787 B2 | 5/2018 | Kane et al. |
| 9,993,654 B2 | 6/2018 | Smith et al. |
| 10,029,107 B1 | 7/2018 | Webb et al. |
| 10,046,167 B2 | 8/2018 | Schmidt et al. |
| 10,065,041 B2 | 9/2018 | Huelskamp et al. |
| 10,092,760 B2 | 10/2018 | Kane et al. |
| 10,137,305 B2 | 11/2018 | Kane et al. |
| 10,159,842 B2 | 12/2018 | Kane et al. |
| 10,213,610 B2 | 2/2019 | Maile et al. |
| 10,220,213 B2 | 3/2019 | Huelskamp et al. |
| 10,226,631 B2 | 3/2019 | Kane et al. |
| 10,238,882 B2 | 3/2019 | Koop |
| 10,279,168 B2 | 5/2019 | Anderson |
| 10,328,272 B2 | 6/2019 | Delanely, Jr. et al. |
| 10,350,423 B2 | 7/2019 | Shuros et al. |
| 10,363,428 B2 | 7/2019 | Smith et al. |
| 10,390,720 B2 | 8/2019 | Anderson et al. |
| 10,391,319 B2 | 8/2019 | Shuros et al. |
| 10,413,733 B2 | 9/2019 | Mi et al. |
| 10,426,962 B2 | 10/2019 | An et al. |
| 10,434,314 B2 | 10/2019 | Ludwig et al. |
| 10,434,317 B2 | 10/2019 | Huelskamp et al. |
| 10,463,305 B2 | 11/2019 | An et al. |
| 10,471,251 B1 | 11/2019 | Manicka |
| 10,512,784 B2 | 12/2019 | Hahn et al. |
| 10,561,330 B2 | 2/2020 | Kharam et al. |
| 10,569,078 B1 | 2/2020 | Manicka |
| 10,569,093 B1 | 2/2020 | Manicka |
| 10,576,291 B2 | 3/2020 | Manicka |
| 10,583,301 B2 | 3/2020 | Haasl et al. |
| 10,589,101 B2 | 3/2020 | Kane et al. |
| 10,617,874 B2 | 4/2020 | Kane et al. |
| 10,632,313 B2 | 4/2020 | Juffer et al. |
| 10,639,483 B2 | 5/2020 | Manicka |
| 10,646,721 B2 | 5/2020 | Manicka |
| 10,668,294 B2 | 6/2020 | Koop et al. |
| 10,674,928 B2 | 6/2020 | Anderson et al. |
| 10,688,304 B2 | 6/2020 | An et al. |
| 10,709,892 B2 | 7/2020 | Kane et al. |
| 10,716,511 B2 | 7/2020 | Manicka |
| 10,716,933 B2 | 7/2020 | Manicka |
| 10,737,102 B2 | 8/2020 | Webb et al. |
| RE48,197 E | 9/2020 | Cho et al. |
| 10,758,724 B2 | 9/2020 | Koop et al. |
| 10,758,737 B2 | 9/2020 | An et al. |
| 10,765,871 B2 | 9/2020 | Kane et al. |
| 10,780,278 B2 | 9/2020 | Hahn et al. |
| 10,821,288 B2 | 11/2020 | Reddy et al. |
| 10,870,008 B2 | 12/2020 | Hahn et al. |
| 10,874,861 B2 | 12/2020 | Koop et al. |
| 10,881,863 B2 | 1/2021 | Maile et al. |
| 10,894,163 B2 | 1/2021 | Stahmann |
| 10,905,872 B2 | 2/2021 | Toy et al. |
| 10,905,886 B2 | 2/2021 | Liu |
| 10,905,889 B2 | 2/2021 | Linder et al. |
| 10,946,202 B2 | 3/2021 | Maile et al. |
| 10,980,481 B2 | 4/2021 | Manicka |
| 10,994,145 B2 | 5/2021 | Koop et al. |
| 11,020,595 B2 | 6/2021 | Koop |
| 11,020,600 B2 | 6/2021 | Schmidt et al. |
| 11,052,258 B2 | 7/2021 | Maile et al. |
| 11,058,880 B2 | 7/2021 | Yang et al. |
| 11,065,459 B2 | 7/2021 | Maile et al. |
| 11,071,870 B2 | 7/2021 | Stahmann et al. |
| 11,083,898 B2 | 8/2021 | Smith et al. |
| 11,123,547 B2 | 9/2021 | Reddy et al. |
| 11,185,703 B2 | 11/2021 | Shuros et al. |
| 11,207,527 B2 | 12/2021 | An et al. |
| 11,207,532 B2 | 12/2021 | Eddy et al. |
| 11,213,676 B2 | 1/2022 | Asleson et al. |
| 11,224,751 B2 | 1/2022 | Huelskamp et al. |
| 11,235,159 B2 | 2/2022 | Yang et al. |
| 11,235,161 B2 | 2/2022 | Ghosh |
| 11,235,163 B2 | 2/2022 | Huelskamp et al. |
| 11,260,216 B2 | 3/2022 | Stahmann et al. |
| 11,285,326 B2 | 3/2022 | Shuros et al. |
| 11,305,125 B2 | 4/2022 | Mi et al. |
| 11,305,127 B2 | 4/2022 | Klepfer et al. |
| 11,400,296 B2 | 8/2022 | Yang et al. |
| 11,464,982 B2 | 10/2022 | Hahn et al. |
| 11,476,927 B2 | 10/2022 | Ludwig et al. |
| 11,478,650 B2 | 10/2022 | Manicka |
| 11,497,921 B2 | 11/2022 | Hahn et al. |
| 11,529,523 B2 | 12/2022 | Balczewski et al. |
| 11,590,353 B2 | 2/2023 | Koop et al. |
| 11,596,798 B2 | 3/2023 | Thacker et al. |
| 11,660,444 B2 | 5/2023 | Manicka |
| 11,679,265 B2 | 6/2023 | Yang et al. |
| 11,697,025 B2 | 7/2023 | Ghosh |
| 11,712,188 B2 | 8/2023 | Ghosh |
| 11,794,026 B1 | 10/2023 | Bardy et al. |
| 11,813,463 B2 | 11/2023 | Stahmann et al. |
| 11,813,464 B2 | 11/2023 | Klepfer et al. |
| 11,813,466 B2 | 11/2023 | Kornet et al. |
| 11,819,699 B2 | 11/2023 | Yang et al. |
| 11,911,168 B2 | 2/2024 | Ghosh |
| 11,951,313 B2 | 4/2024 | Bonner et al. |
| 12,083,348 B2 | 9/2024 | Prutchi |
| 12,151,116 B2 | 11/2024 | Maile et al. |
| 12,172,021 B2 | 12/2024 | Ghosh |
| 12,186,550 B2 | 1/2025 | Manicka |
| 12,233,250 B2 | 2/2025 | Stotz et al. |
| 12,233,265 B2 | 2/2025 | Hamner et al. |
| 12,296,177 B2 | 5/2025 | Grenz et al. |
| 12,337,184 B2 | 6/2025 | Li et al. |
| 2002/0183838 A1 | 12/2002 | Liddicoat et al. |
| 2008/0004904 A1 | 1/2008 | Tran |
| 2010/0179562 A1 | 7/2010 | Linker et al. |
| 2011/0087257 A1 | 4/2011 | To et al. |
| 2013/0060149 A1 | 3/2013 | Song et al. |
| 2015/0343176 A1 | 12/2015 | Asleson et al. |
| 2016/0144192 A1 | 5/2016 | Sanghera et al. |
| 2017/0021159 A1 | 1/2017 | Reddy et al. |
| 2017/0128734 A1 | 5/2017 | Gunderson et al. |

(56)                     References Cited

U.S. PATENT DOCUMENTS

| | | |
|---|---|---|
| 2017/0354827 A1 | 12/2017 | Zhang et al. |
| 2018/0133463 A1 | 5/2018 | Reddy |
| 2018/0243536 A1 | 8/2018 | Von Segesser |
| 2019/0223782 A1 | 7/2019 | Wen et al. |
| 2020/0037888 A1 | 2/2020 | Thakur et al. |
| 2020/0037895 A1 | 2/2020 | Cheng et al. |
| 2020/0038060 A1 | 2/2020 | Nikolski et al. |
| 2021/0031048 A1 | 2/2021 | Marshall et al. |
| 2021/0259560 A1 | 8/2021 | Venkatraman et al. |
| 2021/0299450 A1 | 9/2021 | Bauer et al. |
| 2021/0338168 A1 | 11/2021 | Landman et al. |
| 2022/0015800 A1 | 1/2022 | Nikolski et al. |
| 2022/0161023 A1 | 5/2022 | Manicka |
| 2022/0296906 A1 | 9/2022 | Westphal et al. |
| 2024/0238605 A1 | 7/2024 | Bardy et al. |
| 2024/0335671 A1 | 10/2024 | Bardy et al. |
| 2025/0025705 A1 | 1/2025 | Felix et al. |
| 2025/0025709 A1 | 1/2025 | Felix et al. |
| 2025/0058125 A1 | 2/2025 | Li et al. |
| 2025/0375115 A1 | 12/2025 | Gaskill et al. |
| 2025/0375116 A1 | 12/2025 | Gaskill et al. |
| 2025/0375218 A1 | 12/2025 | Gaskill et al. |

FOREIGN PATENT DOCUMENTS

| | | |
|---|---|---|
| WO | WO-2025038952 A1 | 2/2025 |
| WO | WO-2025166030 A1 | 8/2025 |
| WO | WO-2025198733 A1 | 9/2025 |
| WO | WO-2026006434 A1 | 1/2026 |

OTHER PUBLICATIONS

[Author Unknown] "Creating new possibilities in advanced pressure measurements." MEMS Pressure Sensors, Millar® | OEM Solutions; Millar, Inc. (2017); 2 pages. [Retrieved online] <URL: millarOEM.com/mems>.

[Author Unknown] "Creating new possibilities in advanced pressure measurements." MEMS Pressure Sensors, Millar® | OEM Solutions; Millar, Inc. (2020); 2 pages. [Retrieved online] <URL: millarOEM.com/mems>.

[Author Unknown] "Detect early compartment syndrome". Mikro-Cath™ Compartment Pressure Catheter; Millar, Inc. (2019); 2 pages. [Retrieved online] <URL: millar.com/mikro-cath-compartment>.

[Author Unknown] "TiSense. Making medical devices smarter, long-term." MEMS Pressure Sensors, Millar. | OEM Solutions; Millar, Inc. (2019); 2 pages. [Retrieved online] <URL: millar.com/oem-solutions>.

Basu-Ray et al. "Subcutaneous versus transvenous implantable defibrillator therapy: a meta-analysis of case-control studies." JACC: Clinical Electrophysiology. Dec. 26, 2017;3(13):1475-1483.

International Search Report and Written Opinion for Application No. PCT/US2024/042740, dated Dec. 26, 2024, 23 pages.

International Search Report and Written Opinion for Application No. PCT/US2025/013826, dated Apr. 9, 2025, 12 pages.

International Search Report and Written Opinion for Application No. PCT/US2025/014954, dated Apr. 3, 2025, 19 pages.

Invitation to Pay Additional Fees for Application No. PCT/US2024/042740, dated Oct. 28, 2024, 2 pages.

Moss et al. "Reduction in inappropriate therapy and mortality through ICD programming." New England Journal of Medicine. Dec. 13, 2012;367(24):2275-2283.

Office Action for U.S. Appl. No. 18/529,544, dated Dec. 27, 2024, 33 pages.

Office Action for U.S. Appl. No. 18/529,544, dated Feb. 22, 2024, 17 pages.

Office Action for U.S. Appl. No. 18/529,544, dated Jun. 21, 2024, 27 pages.

Invitation to Pay Additional Fees for Application No. PCT/US2025/035229, dated Aug. 18, 2025, 2 pages.

Hu et al. "Intelligent Sensor Networks, The Integration of Sensor Networks, Signal Processing and Machine Learning." CRC Press, Taylor Francis Group. Oct. 23, 2012: p. 5, 36 total pages.

Huang et al. "Kernel based algorithms for mining huge data sets: Supervised, semi-supervised, and unsupervised learning." Springer. Mar. 2, 2006; 17; p. 1, 18 total pages.

Mitchell TM." The Discipline of Machine Learning." Carnegie Mellon University, School of Computer Science, Machine Learning Department; Jul. 2006; pp. 3-4, 12 total pages.

Nasseri et al. "Clinical and Radiologic Review of the Normal and Abnormal Thymus: Pearls and Pitfalls." Radiographics. Mar. 2010;30(2):413-428.

PCT Application No. PCT/US2025/035229, International Search Report and Written Opinion mailed Oct. 22, 2025; Applicant North American EP Technology LLC; 15 pages.

U.S. Appl. No. 19/300,138, Non-Final Office Action mailed Oct. 28, 2025; Inventor Gaskill, Robert Joseph et al.; 13 pages.

U.S. Appl. No. 19/300,150, Non-Final Office Action mailed Oct. 30, 2025; Inventor Gaskill, Robert Joseph et al.; 59 pages.

U.S. Appl. No. 19/300, 128, Non-Final Office Action mailed Jan. 21, 2026; Inventor Li, Yanhui et al.; 13 pages.

SYSTEMS, DEVICES, AND METHODS FOR IMPROVING PATIENT OUTCOMES IN IMPLANTABLE CARDIOVERTER DEFIBRILLATORS

CROSS-REFERENCE TO RELATED APPLICATIONS

This application is a continuation of U.S. patent application Ser. No. 18/529,544 (now U.S. Pat. No. 12,337,184), filed Dec. 5, 2023, entitled "Systems, Devices, and Methods for Improving Patient Outcomes in Implantable Cardioverter Defibrillators," which claims priority to and the benefit of U.S. Provisional Patent Application No. 63/533,062, filed Aug. 16, 2023, entitled "Systems, Devices, and Methods for Improving Patient Outcomes in Implantable Cardioverter Defibrillators," the disclosure of each of which is incorporated herein by reference in its entirety.

BACKGROUND

The embodiments described herein relate generally to implantable cardioverter defibrillators and more particularly, to systems, devices, and methods for monitoring cardiovascular activity of a patient and applying a corrective action as a treatment for cardiac events.

An implantable cardioverter defibrillator (ICD) is a medical device that is designed to address cardiac tachyarrhythmias using cardiac electrical signals to make ICD therapy decisions automatically by detection algorithm. ICDs have been used for treatment of sudden cardiac arrest, tachycardia arrhythmias, and other issues that lead to sudden cardiac death. One of the consistent challenges of ICDs, however, is the delivery of unnecessary and/or inappropriate ICD therapy. These therapies include a delivered shock or anti-tachycardia pacing (low-energy shocks, also referred to as ATP). Such ICD therapy can be painful or uncomfortable annoyances to a patient and reducing inappropriate shocks has been demonstrated to reduce all-cause mortality in patients using an ICD.

The Cardiac Arrhythmia Suppression Trial (CAST) demonstrated that clinical benefit evaluation needs a desirable clinical end point of related mortality (survival). As a surrogate endpoint, ventricular premature heart beats do not provide a good evaluation of clinical benefit for patient outcomes. For ICDs to make desirable decisions in delivering ICD therapy, these devices also rely on sensitive and specific parameters (sensors) and/or algorithms. To make optimized therapy decisions for patient outcomes, it is desirable for ICDs to mimic clinical practice and/or be based on high quality clinical data. In clinical practice, making an optimum decision to manage an arrhythmia focuses not only on electrocardiogram (ECG) performance and diagnosis, but also on the patient's hemodynamic status and other clinical conditions.

From an engineering point of view, the human heart is a mechanical pump for moving blood through the body and is driven by cardiac electrical activities. Cardiac electrical abnormalities (cardiac electrical signals) result in abnormalities in the mechanical function of the pump, which can result in abnormal heart function. Combination monitoring for mechanical pump dysfunction (hemodynamic monitoring) and electrical abnormalities (cardiac electrical signals) is more direct and accurate than simple monitoring of cardiac electrical signal abnormalities.

Current ICDs simulate ECG-based arrhythmia management decision-making by cardiologists or electrophysiologists using cardiac electrical signals recorded by intravenous or extra-cardiovascular electrodes. Presently, sensed cardiac signals and/or derivations thereof has/have been used as the primary determinant(s) of shock therapy decisions in ICDs. Cardiac signals can include physiological or pathophysiological bio-signals from the heart, such as cardiac electrical signals, cardiac mechanical signals, hemodynamics, and/or the like. The measurement of cardiac electrical signals, for example, includes heart rate, voltage, P wave, QRS morphology, ST segment, T wave, and ECG diagnosis, and/or the like.

One of the challenges with current ICDs, however, is inaccurate therapy decisions due to relatively poor-quality cardiac signals being recorded by ICD electrodes. For example, algorithms using these signals exclusively may classify cardiac events incorrectly as requiring shock therapy, creating false positives and therefore, inappropriate ICD therapies. Inappropriate ICD therapies can lead to increased myocardial damage and increased mortality. In addition, some cardiac events may resolve in a relatively short amount of time without shock therapy and/or may produce cardiac electrical signals that indicate a shock therapy should be delivered without a corresponding change in cardiac mechanical state or hemodynamic output, and providing shock therapy in these situations may also be considered inappropriate ICD therapies. Studies have found that such inappropriate therapies can increase the all-cause mortality associated with the overall ICD therapy for patients and reducing the delivery of such inappropriate ICD therapies (e.g., in response to cardiac electrical states that do not have or result in a corresponding or substantial change in cardiac mechanical state of hemodynamic output) can lead to improved patient outcomes.

In traditional ICD implantation procedures, leads are delivered into the heart transvenously, allowing the leads and sensors thereof to receive relatively clean ECG signals. While these ECG signals are clean (or at least substantially clean), challenges remain in the discrimination of true ventricular rate due to the potential confounding of multiple sources of events that can get classified as high ventricular rates in the ECG signals, without a corresponding or anticipated reduction of hemodynamic output. For example, an ECG signal associated with or otherwise suggesting atrial fibrillation may be classified by the ICD as ventricular tachycardia or an ECG signal associated with or otherwise suggesting noise may be classified as ventricular fibrillation. These misclassifications can lead to inappropriate shocks.

Transvenous delivery of traditional ICD leads, however, can result in patient complications with the transvenous lead that can result in lead-related complications. In an effort to mitigate such complications, subcutaneous and/or substernal ICDs have been developed that use leads and/or sensing electrodes that are placed external to the heart, but such placement can increase pacing thresholds compared to intravenous ICDs. These high pacing thresholds prohibit or limit the ability of subcutaneous ICDs to leverage anti-tachycardia pacing to treat spontaneous ventricular tachycardia without triggering a painful, high-energy shock that may be considered inappropriate. Moreover, relying on only cardiac signals as the primary determinant of shock therapy decisions, whether using traditional or subcutaneous/substernal ICDs, can result in false positives that can lead to the ICD activating and delivering an unnecessary/inappropriate shock to the patient. Thus, there is a need to decrease false positives in ICDs and reduce patient complications.

SUMMARY

In some embodiments, a method is for improving treatment decisions of an implantable cardioverter defibrillator

3

(ICD) implanted in a patient. The method includes determining an electrical status of a heart of the patient based on a first signal received from an electrical sensor of an ICD lead that is implanted in an anterior mediastinum of the patient. The electrical sensor is configured to detect electrical signals radiating from the heart. The method includes calculating a hemodynamic output of the heart based on a second signal received from a pressure sensor of the ICD lead. The pressure sensor is configured to detect pressure changes in the anterior mediastinum due to a mechanical functioning of the heart. The method includes defining a treatment decision based on a correlation between the electrical status and the hemodynamic output of the heart.

In some embodiments, a non-transitory processor-readable medium stores code representing instructions to be executed by a processor. The code includes code to cause the processor to determine an electrical status of a heart of a patient based on a first signal received from an electrical sensor of an ICD lead that has been implanted in an anterior mediastinum of a patient. The electrical sensor is configured to detect electrical signals radiating from the heart. The code includes code to cause the processor to calculate a hemodynamic output of the heart based on a second signal received from a pressure sensor of the ICD lead. The pressure sensor is configured to detect pressure changes in the anterior mediastinum due to a mechanical functioning of the heart. The code includes code to cause the processor to define a treatment decision based on a correlation between the electrical status and the hemodynamic output of the heart.

In some embodiments, a system includes an electrical sensor coupled to a lead configured to be implanted in an anterior mediastinum of a patient. The electrical sensor is configured to detect electrical signals radiating from a heart of the patient. The system includes a pressure sensor coupled to the lead. The pressure sensor is configured to detect pressure changes in the anterior mediastinum due to a mechanical functioning of the heart. The system includes an implantable cardioverter defibrillator (ICD) configured to be implanted in the patient. The ICD includes a generator coupled to the lead when the lead is implanted in the anterior mediastinum. The generator includes a memory and a processor configured to execute instructions stored in the memory operable to cause the processor to determine an electrical status based on a first signal received from the electrical sensor, calculate a hemodynamic output of the heart based on a second signal received from the pressure sensor, and define a treatment decision based on a correlation between the electrical status and the hemodynamic output of the heart.

In some embodiments, a method is for improving treatment decisions of an implantable cardioverter defibrillator (ICD) implanted in a patient. The method includes determining an electrical status based on a first signal received from an electrical sensor of an ICD lead implanted in an anterior mediastinum of a patient. The electrical sensor is configured to detect electrical signals radiating from a heart of the patient. The method includes determining a hemodynamic output of the heart based on a second signal received from a pressure sensor coupled to the ICD lead. The pressure sensor is configured to detect pressure changes in the anterior mediastinum due to a mechanical functioning of the heart. The method includes, responsive to each of the electrical status and the hemodynamic output being associated with a cardiac arrhythmia, causing a generator of the ICD to generate a treatment energy to be delivered via the ICD lead to the heart of the patient.

4

DETAILED DESCRIPTION

Figure 1:
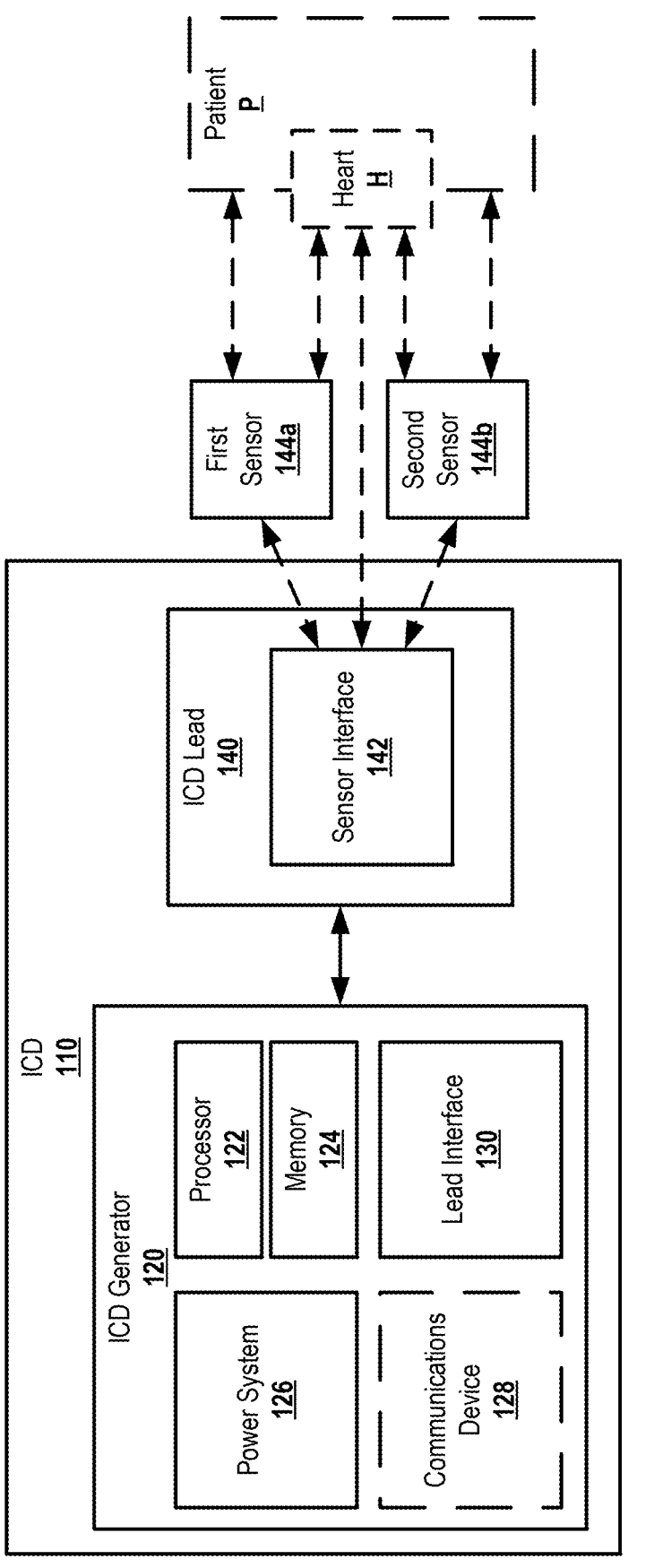
FIG. 1 schematically depicts an implantable cardioverter defibrillator (ICD) engaging with a patient according to an embodiment.

The embodiments described herein relate generally to systems, devices, and/or methods for monitoring and/or detecting cardiovascular activity to decrease a likelihood of undesirable, incorrect, and/or inappropriate ICD detection or ICD therapy decision(s). In some embodiments, an ICD may be configured to deliver shock therapy based at least in part on one or more characteristics associated with a heart of a patient. For example, the ICD can include and/or can be in communication with any number of sensors configured to detect one or more characteristics associated with the heart. The one or more characteristics can also include characteristics that are not detected by the sensors, such as patient demographic and/or health data (e.g., age, genetic information, health records, etc.). The one or more characteristics can be correlated and used to determine whether to provide treatment. In some implementations, correlating data associated with the one or more characteristics can reduce undesirable ICD decision(s) by confirming that an irregular heart event is occurring when an irregularity is determined based on one of the characteristics.

In some embodiments, an ICD can include and/or can be in communication with one or more sensors configured to detect at least two characteristics associated with the heart. For example, a first characteristic can be cardiac signals and/or one or more derivatives thereof, which can be determined based at least in part on data from one or more sensors (e.g., one or more sensors used for detecting cardiac electrical signals, referred to generally as an "ECG sensor"). In this manner, the first characteristic can be similar to and/or substantially the same as the cardiac electrical signals that are used in known ICDs. As described above, using cardiac electrical signals alone to make decisions on whether to provide treatment can lead to undesirable, incorrect, and/or inappropriate ICD detection and/or therapy decisions. Accordingly, the devices, systems, and/or methods described herein are configured to correlate, aggregate, combine, analyze, and/or process the first characteristic, or data used to determine the first characteristic, with any other suitable characteristic(s) (or data) associated with the heart (or more generally, the patient) to determine if the heart is having an irregular and/or adverse event such as, for example, tachycardia, ventricular fibrillation, sudden cardiac arrest, etc. For example, such a process of correlating characteristics and/or data can include determining whether a cardiac rhythm seen in cardiac electrical signal data has an expected corresponding result in the hemodynamic status and/or output signal data. In such examples, it may be determined to withhold ICD therapy if a potential irregular cardiac rhythm is detected without a corresponding irregular hemodynamic status and/or output.

In some implementations, the other characteristic(s) and/or data can be, for example, hemodynamic status as measured by one or more sensors directly or indirectly. For example, one or more sensors can be a pressure sensor, transducer, etc. configured to measure changes in pressure. In some implementations, the sensor(s) can be configured to directly measure and/or detect hemodynamic status or a pressure associated with the hemodynamic status (e.g., blood pressure). In some implementations, the sensor(s) can be configured to indirectly measure and/or detect hemodynamic status or a pressure associated with the hemodynamic status. For example, in some embodiments, an ICD can be in communication with one or more pressure sensors, transducers, and/or the like (referred to generally as "pressure sensor"), which is in contact with and/or in close proximity to free wall of either the right, left, or both ventricles. In such embodiments, movement associated with the pumping/beating of the heart can result in pressure changes in the tissue or volumes surrounding the heart, which in turn, can be measured and/or detected by the pressure sensor.

In some implementations, inputs from the pressure sensor (and/or any other sensor) can be used and/or correlated with inputs of the ECG sensor to detect and/or determine a cardiac status and/or the occurrence of health events, such as arrhythmia, tachycardia, and/or the like. The cardiac status determined using the methods described herein can be more specific than determining cardiac status using cardiac signal measurements alone, hemodynamic status measurements alone, and/or other cardiac characteristics individually. For example, because incorrectly withholding ICD therapy (false negative) is more harmful than incorrectly providing ICD therapy (false positive), and therefore, current ICDs using only cardiac signal measurements are typically designed with greater sensitivity and less specificity. Using a combination of cardiac signal measurements such as cardiac electrical signal measurements and cardiac mechanical signal measurements (e.g., hemodynamic rate, status, and/or output measurements) can increase sensitivity and specificity, thereby reducing false results (false positives and false negatives). Additionally, detecting, sensing, and/or determining hemodynamic status can further confirm ventricular tachycardia, ventricular fibrillation, and/or other cardiac states. This results in specificity in ICD therapy decisions that is more beneficial to patients and supported by clinical evidence. In some implementations, anti-tachycardia pacing and/or shock treatment decisions can be made based on the signals from the one or more sensors (e.g., cardiac electrical signal measurements and/or cardiac mechanical signal measurements) and/or the correlated data associated therewith (e.g., ex vivo data such as patient demographic and/or health data-age, weight, cardiac pathology, genetic information, health records, etc.).

In some embodiments, systems, devices, and/or methods described herein can be used, inter alia, to reduce undesired and/or inappropriate treatments provided by an ICD implanted in a patient (e.g., a transvenous ICD, subcutaneous ICD, and/or substernal ICD). For example, in some implementations, a method of providing treatment using an ICD can include receiving first signal data and second signal data associated with at least one characteristic of a heart of the patient and determining a cardiac status based at least in part on the first signal data and the second signal data. In some embodiments, the first signal data can be received from a first sensor and the second signal data can be received from a second sensor. In some embodiments, the first sensor can be configured to sense a first characteristic of the heart and the second sensor can be configured to sense a second characteristic of the heart, different from the first characteristic. The method further includes determining, based on the cardiac status, if a health event is occurring and, responsive to determining that a health event is occurring, applying a treatment to heart of the patient.

The terminology used herein is for the purpose of describing particular embodiments, implementations, and/or concepts (including any feature(s) or aspect(s) thereof) and is not intended to be limiting. Unless defined otherwise, technical and/or scientific terms used herein have the same meanings as commonly understood by one of ordinary skill in the art. Any explanation or discussion of or using particular terms is intended to provide context and to facilitate understanding and is not necessarily intended to replace or supersede commonly used or known definitions understood by one skilled in the art unless explicitly stated otherwise. Moreover, various terms may be used to describe similar or substantially the same embodiments, implementations, and/or concepts (including any feature(s) or aspect(s) thereof) and thus, the use of particular term is not intended to be limiting and/or to the exclusion of other terms unless terms are mutually exclusive, or the context clearly states otherwise.

As used herein, the singular forms "a," "an," and "the" are intended to include the plural forms as well, unless the context clearly indicates otherwise. With respect to the use of singular and/or plural terms herein, those having skill in the art can translate from the singular to the plurality and/or vice versa as is appropriate for the context and/or application. Furthermore, any reference herein to a singular component, feature, aspect, etc. is not intended to imply the exclusion of more than one such component, feature, aspect, etc. (and/or vice versa) unless expressly stated otherwise. The various singular/plural permutations may be expressly set forth herein for sake of clarity.

In general, terms used herein and in the appended claims are intended as "open" terms unless expressly stated otherwise. For example, the term "including" should be interpreted as "including but not limited to," the term "having" should be interpreted as "having at least," etc. Similarly, the term "comprising" may specify the presence of stated features, elements, components, integers (or fractions thereof), steps, operations, and/or the like but does not preclude the presence or addition of one or more other features, elements, components, integers (or fractions thereof), steps, operations, elements, components, and/or groups thereof, and/or the like unless such combinations are otherwise mutually exclusive.

As used herein the term "and/or" includes any and all combinations of one or more of the associated listed items. It should be understood that any suitable disjunctive word and/or phrase presenting two or more alternative terms, whether in the written description or claims, contemplate the possibilities of including one of the terms, either of the terms, or both/all of the terms. For example, the phrase "A and/or B" will be understood to include the possibilities of "A" alone, "B" alone, or a combination of "A and B."

All ranges described herein include each individual member or value and are intended to encompass any and all possible subranges and/or combinations of subranges thereof unless expressly stated otherwise. Any listed range should be recognized as sufficiently describing and enabling the same range being broken down into at least equal subparts unless expressly stated otherwise.

As used herein, the terms "about," "approximately," and/or "substantially" when used in connection with stated value(s) and/or geometric structure(s) or relationship(s) is intended to convey that the value or characteristic so defined is nominally the value stated or characteristic described. In some instances, the terms "about," "approximately," and/or "substantially" can generally mean and/or can generally contemplate a value or characteristic stated within a desirable tolerance (e.g., plus or minus 10% of the value or characteristic stated). For example, a value of about 0.01 can include 0.009 and 0.011, a value of about 0.5 can include 0.45 and 0.55, a value of about 10 can include 9 to 11, and a value of about 1000 can include 900 to 1100. Similarly, a first surface may be described as being substantially parallel to a second surface when the surfaces are nominally parallel. While a value, structure, and/or relationship stated may be desirable, it should be understood that some variance may occur as a result of, for example, manufacturing tolerances or other practical considerations (such as, for example, the pressure or force applied through a portion of a device, conduit, lumen, etc.). Accordingly, the terms "about," "approximately," and/or "substantially" can be used herein to account for such tolerances and/or considerations.

As used herein, the words "proximal" and "distal" refer to the direction closer to and away from, respectively, a user who would place the device into contact with a patient. The words "proximal" or "distal" can be relative terms and do not necessarily refer to universally fixed positions or directions. Thus, for example, the end or end portion of a device first touching the body of the patient would be the distal end or distal end portion, while the opposite end or end portion of the device (e.g., the end or end portion of the device being manipulated by the user) would be the proximal end or proximal end portion of the device.

As used herein, the term "cardiac signals" generally refers to signals from one or more sensors that can include physiological or pathophysiological bio-signals from the heart. Such signals can be, for example, cardiac electrical signals or cardiac non-electrical signals. Cardiac electrical signals can include any suitable signals associated with and/or otherwise indicative of the electrical functioning of the heart. The measurement of such cardiac electrical signals may include, but is not limited to, heart rate, voltage, P wave, QRS morphology, ST segment, T wave, ECG diagnosis, and/or the like, sensed through any suitable number of vectors. Cardiac non-electrical signals (also referred to herein as "cardiac mechanical signals") can include any suitable signals associated with and/or otherwise indicative of the non-electrical (e.g., mechanical) functioning of the heart. The measurement of such cardiac mechanical signals may include, but is not limited to, pressure characteristics (e.g., blood pressure, pressure in the tissue or volumes surrounding the heart, venous pressures, arterial pressures, and/or changes in such pressures, etc.), hemodynamic characteristics, oxygen saturation, sensed mechanical heart movement, cardiac sounds, cardiac echogram (ultrasound), cardiac Doppler, and/or the like.

The embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include but are not necessarily limited to metals, glasses, ceramics, and/or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides, polyanhydrides, polyorthoesters, polyetheresters, polycaprolactones, polyesteramides, poly(butyric acid), poly(valeric acid), polyurethanes, biodegradable polyamides (nylons), and/or blends and copolymers thereof. Examples of non-biodegradable polymers include non-degradable polyamides (nylons), polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

Non-limiting examples of suitable biocompatible polymer materials can include polylactides, polyglycolides, polylactide-co-glycolides, polyethylene-glycols, polyanhydrides, polyorthoesters, polyetheresters, polycaprolactones, polyesteramides, poly(butyric acid), poly(valeric acid), polyurethanes, polyamides (nylons), polyesters, polycarbonates, polyacrylates, polystyrenes, polypropylenes, polyethylenes, polyethylene oxide, polyolefins, polyethersulphones, polysulphones, polyvinylpyrrolidones, polyvinyl chloride, polyvinyl fluoride, poly(vinyl imidazole), polyether urethanes, silicone polyether urethanes, polyetheretherketones (PEEK), polytetrafluoroethylenes (PTFE), polylactones, chlorosulphonate polyolefins, ethylene-vinyl acetates and other acyl substituted cellulose acetates, elastomers, thermoplastics, and/or blends and copolymers thereof.

The embodiments, methods, and/or implementations herein, and/or the various features or advantageous details thereof, are explained more fully with reference to the non-limiting examples illustrated in the accompanying drawings and detailed in the following description. The examples and/or embodiments described herein are intended to facilitate an understanding of structures, functions, and/or aspects of the embodiments, ways in which the embodiments may be practiced, and/or to further enable those skilled in the art to practice the embodiments herein. Similarly, methods and/or ways of using or implementing the embodiments described herein are provided by way of example only and not limitation. Specific uses and/or implementations described herein are not provided to the exclusion of other uses unless the context expressly states otherwise. Descriptions of well-known components, methods, techniques, etc. may be omitted so as to not obscure the embodiments herein. Like numbers refer to like elements throughout.

FIG. 1 schematically depicts an implantable cardioverter defibrillator (ICD) system 100 including an ICD 110 engaging a patient P according to an embodiment. The ICD 110 is implanted (or implantable) in the patient P. The ICD system 100 can be utilized for treating certain conditions or states of a heart H of the patient P via certain electric treatment therapies, while reducing a likelihood of providing undesired, unnecessary or inappropriate treatments (e.g., "false positives"). The ICD 110 includes an ICD generator 120 and an ICD lead 140. The ICD system 100 further includes a first sensor 144a and a second sensor 144b in communication with the ICD 110.

While the ICD system 100 is described herein as including "the first sensor 144a" and "the second sensor 144b," it should be understood that the first sensor 144a can be a single sensing device or multiple sensing devices that collectively function as the first sensor 144a, and similarly, the second sensor 144b can be a single sensing device or multiple sensing devices that collectively function as the second sensor 144b. In some implementations, multiple sensing devices can allow for sensor data that includes multiple signal vectors (e.g., multiple cardiac electrical and/or mechanical signal vectors). Similarly, while the ICD system 100 is described herein as including "the first sensor 144a" and "the second sensor 144b," it should be understood that the ICD system 100 can include any number of additional sensors configured to sense and/or detect any suitable characteristic(s) associated with the patient (e.g., cardiac electrical and/or mechanical signals or any suitable noncardiac signals). In some implementations, each sensor can be configured to sense and/or detect a different characteristic associated with the heart, or more generally, the patient. In some implementations, one or more sensors can be configured to sense or detect the same characteristic, thereby allowing for confirmation/verification of signal data and/or a desired degree of sensitivity and/or specificity in interpreting the signal data.

The ICD 110 is configured to receive signals from the first sensor 144a and the second sensor 144b associated with one or more characteristics of the patient P or the heart H of the patient P. In some embodiments, the ICD 110 can receive multiple signals from one or both of the first sensor 144a and the second sensor 144b. The ICD 110 includes the ICD generator 120, which can include a processor 122, a memory 124, a power system 126, a communication device 128, and a lead interface 130. The ICD generator 120 is configured to determine when to provide treatment and to generate treatment energy that can be sent to the heart H via the ICD lead 140. In some embodiments, the ICD generator 120 can be placed on the pectoralis major muscle of the patient P, behind the pectoral major muscle, on the abdomen, along the left exterior thorax, or elsewhere on or in the body of the patient P.

The processor 122 is configured to execute the operations of the ICD generator 120. The processor 122 can be, for example, a hardware based integrated circuit (IC), or any other suitable processing device configured to run and/or execute a set of instructions or code. For example, the processor 122 can be a general-purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC), and/or the like. The processor 22 can be operatively coupled to the memory 124 through a system bus (for example, address bus, data bus, and/or control bus).

The memory 124 stores instructions that are executed by the processor 122. The memory 124 can be, for example, a random-access memory (RAM), a memory buffer, a hard drive, a read-only memory (ROM), an erasable programmable read-only memory (EPROM), and/or the like. In some instances, the memory 124 can store, for example, one or more software programs and/or code that can include instructions to cause the processor 122 to perform one or more processes, functions, and/or the like. In some implementations, the memory 124 can include extendable storage units that can be added and used incrementally. In some instances, the memory 124 can be remotely operatively coupled with a compute device (not shown). For example, a remote database device can serve as a memory (or at least a portion of a memory) and be operatively coupled to the compute device (e.g., via a network or the like).

The memory 124 can, for example, include instructions on determining when treatment should be applied to the heart of the patient P. The memory 124 can include instructions that can cause the processor 122 to analyze sensor data received from the first sensor 144a and/or the second sensor 144b and to determine and/or define one or more treatment characteristics, modalities, methods, etc. These instructions can be updated and/or refined based on learnings from previously received sensor data. The memory 124 can further include instructions for managing the power usage of the power system 126, which can be configured to apply or provide electrical power (e.g., shock) according to the treatment characteristics, modalities, methods, etc., determined and/or defined by the processor 122.

The processor 122 is configured to execute instructions stored in the memory 124. More specifically, the memory 124 can, in some embodiments, include instructions associated with preprocessing the signals from the first sensor 144a and the second sensor 144b. For example, the memory 124 can include and/or store instructions that when executed by the processor 122 perform one or more preprocessing steps that can include amplification, filtering, analog to digital conversion, signal recognition and detection, synchronization, and/or the like. The processor 122 is configured to execute instructions, stored and/or included in the memory 124, for determining a cardiac status based on the signals, with or without preprocessing. The cardiac status can be associated with a heartbeat, an output of the heart, sensor data, and/or the like. Determining the cardiac status can include comparing an output from the first sensor 144a and an output from the second sensor 144b to recognize and confirm cardiac activity. For example, if the output from the first sensor 144a appears to indicate an irregular heartbeat, but the output from the second sensor 144b does not appear to indicate an irregular heartbeat, then the output from the first sensor 144a may be determined to be a false positive. Determining false positives can allow the ICD 110 to decrease the number of undesired treatments for the patient P and is more specific than if using an output from just one of the first sensor 144a or the second sensor 144b. If both the first sensor 144a and the second sensor 144b indicate the same and/or complementary cardiac status, that cardiac status is determined and/or confirmed. For example, in some embodiments, the memory 124 can include instructions associated with correlating heart rate data (e.g., from the first sensor 144a) and hemodynamic output or status data (e.g., from the second sensor 144b).

In some embodiments, determining the cardiac status can utilize an artificial intelligence algorithm (e.g., a machine learning model and/or algorithm) to further refine, determine, and/or predict the cardiac status. For example, the machine learning model can be trained to determine the cardiac status based at least in part on cardiac signal data and hemodynamic status data. In some embodiments, the machine learning model and/or algorithm (referred to herein as machine learning "model" or "algorithm" interchangeably) can be configured to filter out or recognize heartbeats and/or other cardiac activity that were determined or missed during an initial determination. In some embodiments, the machine learning algorithm can correlate the outputs from the first sensor 144a and the second sensor 144b to determine a pattern corresponding to a cardiac rate, status, QRS complex, etc. In some embodiments, the machine learning algorithm can learn from the outputs of the first sensor 144a and the second sensor 144b to determine long-term correlation and changes in correlation between the output of the first sensor 144a and the second sensor 144b.

The processor 122 may be configured to execute instructions, stored and/or included in the memory 124, associated with determining if a health event (e.g., an adverse health event that may be undesirable or dangerous to the patient such as, for example, cardiac arrest, ventricular fibrillation, cardiac tamponade, tachycardia, and/or other cardiac electrical or mechanical pathologies) is occurring based on the cardiac status. The health event can correspond to at least one of cardiac attack, tachycardia, fibrillation, arrythmias, and/or the like. In some embodiments, the processor 122 may execute a machine learning algorithm, which may be the same or different than that used in refining, determining, and/or predicting the cardiac status, for determining if a health event is occurring. The memory 124 can further include and/or store instructions for execution by the processor 122 associated with determining the type of health event. For example, the processor 122 determining the type of health event can include correlating the cardiac status with known cardiac statuses associated with health events. In some embodiments, the memory 124 can further include and/or store instructions for determining if the health event is an adverse health event. Similarly stated, the memory 124 can include and/or store instructions for determining and/or distinguishing an adverse health event from, for example, a normal or non-adverse health event that may present and/or may be associated with one or more similar characteristics.

In some embodiments, the processor 122 can determine the type of adverse health event (e.g., any of the adverse health events described herein). In some embodiments, the processor 122 may execute one or more machine learning algorithms, which may be the same or different than the other machine learning algorithms described herein, for determining the type of health event. Based on the type of health event determined, the memory 124 may store and/or include instructions for execution by the processor 122 associated with determining a treatment based on the type of health event. For example, the memory 124 may store and/or include instructions associated with determining the treatment based on the type of adverse health event. For example, if the adverse health event is determined to be tachycardia, then the treatment may correspond to anti-tachycardia pacing. The memory 124 can store and/or include instructions for execution by the processor 122 associated with determining the type of treatment as well as specific parameters for the treatment based on the adverse health event and, optionally, any other information (e.g., patient information, cardiac status, sensor signals, etc.). The memory 124 further stores and/or includes instructions for execution by the processor 122 for applying the treatment to the heart H of the patient P. This can include instructions for commanding and/or at least partially controlling the ICD to deliver the treatment to the heart H of the patient P (e.g., via the power system 126). In some embodiments, the memory 124 can store and/or include instructions that cause the processor 122 to alter or pause treatment during treatment delivery based on outputs from the first sensor 144a and the second sensor 144b. In some embodiments, the memory 124 can store and/or include instructions that cause the processor 122 to operate the generator to generate the treatment energy based on the type, severity, duration, and/or other characteristic(s) of an adverse health event.

The power system 126 is configured to store energy for use by the ICD and to generate treatments for delivery to the patient P. In some embodiments, the power system 126 can include at least one battery (e.g., LiPo, Li-ion, etc.). The at least one battery can be charged when the battery is low on power. In some embodiments, the power system 126 includes a primary cell battery and a rechargeable battery. In some embodiments, the power system 126 can be configured to charge automatically (e.g., via patient P movement) or wirelessly (e.g., via inductive charging). The power system 126 can also be configured to generate a therapy signal (e.g., anti-tachycardia pacing, defibrillator shock, etc.). For example, the therapy signal can include treatment energy for at least one of anti-tachycardia pacing and/or shock therapy. In some implementations, the treatment energy for anti-tachycardia pacing can be low-power or relatively low-power treatment energy and the treatment energy for shock therapy can be high-power or relatively high-power treatment energy. In some embodiments, the operation of the power system 126 is controlled via the processor 122 executing instructions stored in the memory 124. In some embodiments, the processor 122 may execute instructions that result in the power system 126 cycling the power of the first sensor 144a and/or the second sensor 144b to conserve power.

The communication device 128 is configured to allow the ICD generator 120 to communicate with one or more devices such as, for example, an external device, an implantable device, controller, server, etc. (e.g., a compute device, controller, etc. of a medical professional, the patient P, and/or the like). The communication device 128 can be configured to send information via one or more networks using any suitable communication mode (e.g., Bluetooth, Wi-Fi, near field communication (NFC), and/or the like). The communication device 128 can be configured to send information with a wired or wireless communication device. In some embodiments, the communication device 128 may be optional.

In some implementations, the communication device 128 can send information to a user and/or a compute device controlled by a user regarding the ICD 110 such as battery level, information regarding therapies delivered to the heart H of the patient P, device status, and/or the like. The communication device 128 can also send information regarding the patient P, such as real-time or substantially real-time information, data, and/or other signals associated with the heart H (e.g., data from the first sensor 144a and/or the second sensor 144b, and/or any other suitable data). In some embodiments, the communication device 128 can receive signals for augmenting and/or at least partially controlling the operation of the ICD 110. For example, the communication device 128 can receive signals (e.g., from a controller or external compute device) associated with patient information and/or other operational instructions for determining when the ICD generator 120 generates a therapy, power levels associated with therapy, pacing and/or other thresholds for anti-tachycardia therapy, and/or the like. In some embodiments, the communication device 128 can be configured to send information and/or signals to an external compute device and/or server that is/are configured to perform machine learning processes. The communication device 128 can also receive information from the external compute device and/or the server that may include instructions, firmware, updates, etc. based on an output from a machine learning model. An example of an external compute device is described in further detail in reference to FIG. 5.

The ICD lead 140 is operatively coupled to the ICD generator 120 via the lead interface 130. The lead interface 130 is configured to couple (e.g., physically couple or at least operably couple) the ICD generator 120 to the ICD lead 140 to allow data signals and/or electric power (e.g., for therapy) to be transferred therebetween. In some embodiments, the lead interface 130 can be configured to format data signals and/or electric power transferred between the ICD generator 120 and the ICD lead 140 into any suitable format allowing, for example, the processing of sensor data or the like by the ICD generator 120 and/or the application of therapy by the ICD lead 140. The lead interface 130 may be a flexible interface to provide flexibility for the continuous movement of the heart and allowing the ICD lead 140 to maintain contact with the heart.

In some embodiments, the ICD lead 140 can extend away from the ICD generator 120 via a conduit that includes a signal/power carrying wire. The ICD lead 140 is configured to deliver treatment to the patient P and/or the heart H of the patient P. As shown in FIG. 1, the ICD lead 140 includes, is operably coupled to, and/or is in communication with the first sensor 144a and the second sensor 144b via a sensor interface 142. For example, the sensors 144a and/or 144b can be included and/or coupled along one or more portions of the ICD lead 140. The sensor interface 142 is configured to communicate with the sensors 144a, 144b to send and/or receive signals between the sensors 144a and 144b, and the ICD lead 140, which in turn is in communication with the ICD generator 120. Alternatively, in some embodiments, the sensors 144a and 144b can be in communication with the lead interface 130 and/or otherwise can be directly in communication with the ICD generator 120. Additionally, in some embodiments, the sensor interface 142 provides the first sensor 144a and the second sensor 144b with power. In some embodiments, the sensor interface 142 can preprocess signals output by and/or received from the first sensor 144a and the second sensor 144b. In some embodiments, the outputs of the sensor interface 142 and/or the first sensor 144a and/or the second sensor 144b can be calibrated based on the patient P, the position in the body of the patient P, and/or the like. For example, the first sensor 144a and/or the second sensor 144b can be calibrated based on one or more known measurement(s) of patient characteristic(s). Calibration can include calibrating the output of the sensors 144a and 144b to align with known measurements of patient characteristics. For example, a cardiac electrical signal sensor used to measure, for example, cardiac rate can be calibrated based on comparing and adjusting the sensor output to an external cardiac rate measuring device.

The ICD lead 140 can include shocking elements for delivering treatment (e.g., including energy from the generator) to the heart H of the patient P. In some embodiments, the ICD lead 140 is positioned substernal in the patient P. In some embodiments, the ICD lead 140 is positioned in contact with, adjacent to, and/or otherwise in close proximity to the fibrous pericardium of the heart H. In some embodiments, the ICD lead 140 can be positioned endocardial, epicardial, or under the sternum. In some embodiments, the ICD lead 140 can be designed and/or formed to use, traverse, and/or fill (or at least substantially use, traverse, and/or fill) at least a portion of the volume between the sternum and the pericardium of the heart H.

The first sensor 144a and the second sensor 144b are configured to measure different health characteristics associated with the heart of the patient P. In some embodiments, the first sensor 144a and the second sensor 144b can measure continuously, periodically, or when a command is received by the first sensor 144a and the second sensor 144b (e.g., received from the processor 122). In some embodiments, the first sensor 144a is configured to measure cardiac signals. In some embodiments, the first sensor 144a is configured to measure cardiac electrical signals (e.g., heart rate, voltage, P wave, QRS morphology, ST segment, T wave, ECG signals, etc.) In some embodiments, the first sensor 144a can be positioned so that it engages the heart H of the patient P and/or in or on the body of the patient P such that the cardiac signals can be measured (e.g., in contact with or in close proximity to the pericardium).

In some embodiments, the second sensor 144b is a different sensor than the first sensor 144a. In some embodiments, the second sensor 144b is configured to measure cardiac mechanical signal data. In some embodiments, the second sensor 144b is configured to measure hemodynamic status. In some embodiments, the second sensor 144b is a pressure sensor. For example, the second sensor 144b may be a pressure sensor configured to measure hemodynamic pressure. In some embodiments, the second sensor 144b is a pressure sensor configured to measure pressure or changes in pressure in the substernal space associated with cardiac movement. In some embodiments, the second sensor 144b is a pressure sensor in a hermetically sealed housing. In some embodiments, the second sensor 144b can be positioned so that it engages the heart H (e.g., the pericardium) of the patient P or can be positioned in any other place in or on the body of the patient P where the second sensor 144b can measure hemodynamic status. In some embodiments, the second sensor 144b is in the anterior mediastinum to measure hemodynamic status.

In some embodiments, the first sensor 144a and/or the second sensor 144b is/are located in the epicardium of the heart. In some embodiments, the first sensor 144a and/or the second sensor 144b is/are located within the heart. For example, the first sensor 144a and/or the second sensor 144b may be located in the right heart. In some embodiments, the first sensor 144a and the second sensor 144b can be collocated or substantially collocated. In some embodiments, the first sensor 144a and/or the second sensor 144b can be remotely or separately located. For example, in some embodiments, the first sensor 144a can be positioned in contact with or adjacent to the fibrous pericardium of the heart H, while the second sensor 144b can be positioned apart from the heart H in the substernal space. In some embodiments, the first sensor 144a and/or the second sensor 144b measures characteristics of the heart H and/or other portions or body parts of the patient P.

As described in further detail herein, the sensors 144a and 144b can measure, detect, and/or sense one or more characteristics associated with the heart H and can send data associated with those characteristics to the ICD generator 120 (e.g., directly or indirectly via the ICD lead 140). Upon receipt, the ICD generator 120 can analyze, process, aggregate, correlate, etc. the data to determine, for example, a cardiac status of the heart H. Furthermore, based on the determined and/or defined cardiac status, the ICD generator 120 can detect and/or determine the occurrence of health events, such as arrhythmia, tachycardia, and/or the like. In some implementations, the use of data from each of the first sensor 144a and the second sensor 144b can allow the ICD generator 120 to determine the cardiac status of the heart H with greater sensitivity and specificity than when determining cardiac status using cardiac signals, QRS complex morphology, and/or other cardiac electrical signal measurements alone (e.g., determined based on signals from the first sensor 144a), hemodynamic status measurements alone (e.g., determined based on signal from the second sensor 144b), and/or other cardiac characteristics individually.

In some implementations, the process of the ICD generator 120 determining the cardiac status and/or functioning of the heart can include, for example, comparing, correlating, and synchronizing the signal data received from the first sensor 144a and the second sensor 144b. For example, the first sensor 144a can be configured to determine and/or sense cardiac electrical signals and the second sensor 144*b* can be configured to determine and/or sense cardiac mechanical signals such as, for example, hemodynamic status and/or output. The ICD generator 120 can receive the signal data from the sensors 144*a* and 144*b* and can determine the cardiac status and further classify cardiac arrhythmia, based at least in part on comparing, correlating, and/or synchronizing a cardiac electrical signal curve (from the first sensor 144*a*) and a cardiac mechanical signal curve (from the second sensor 144*b*). Thus, determining a cardiac status and a classification of cardiac arrhythmia can include the ICD generator 120 determining whether a sensed or determined cardiac rhythm (e.g., based on cardiac electrical signal data received from the first sensor 144*a*) has an expected corresponding sensed or determined hemodynamic status and/or output (e.g., based on cardiac mechanical signal data received from the second sensor 144*b*). If a hemodynamic status and/or output is not what is expected, based on the determined cardiac rhythm), the ICD generator 120 may withhold, delay, and/or modify the ICD therapy. In some embodiments, one or more machine learning algorithms may be employed to define, determine, and/or correlate expected hemodynamic status(es) and/or output(s) for a given cardiac rhythm. In some embodiments, one or more machine learning algorithms may be employed to define, determine, correlate, and/or predict a cardiac status based at least in part on one or more relationships and/or a degree of correlation between, for example, data received from the first sensor 144*a* (e.g., cardiac electrical signal data such as, for example, cardiac rhythm) and data received from the second sensor 144*b* (e.g., cardiac mechanical signal data such as, for example, hemodynamic status and/or output).

Figure 2:
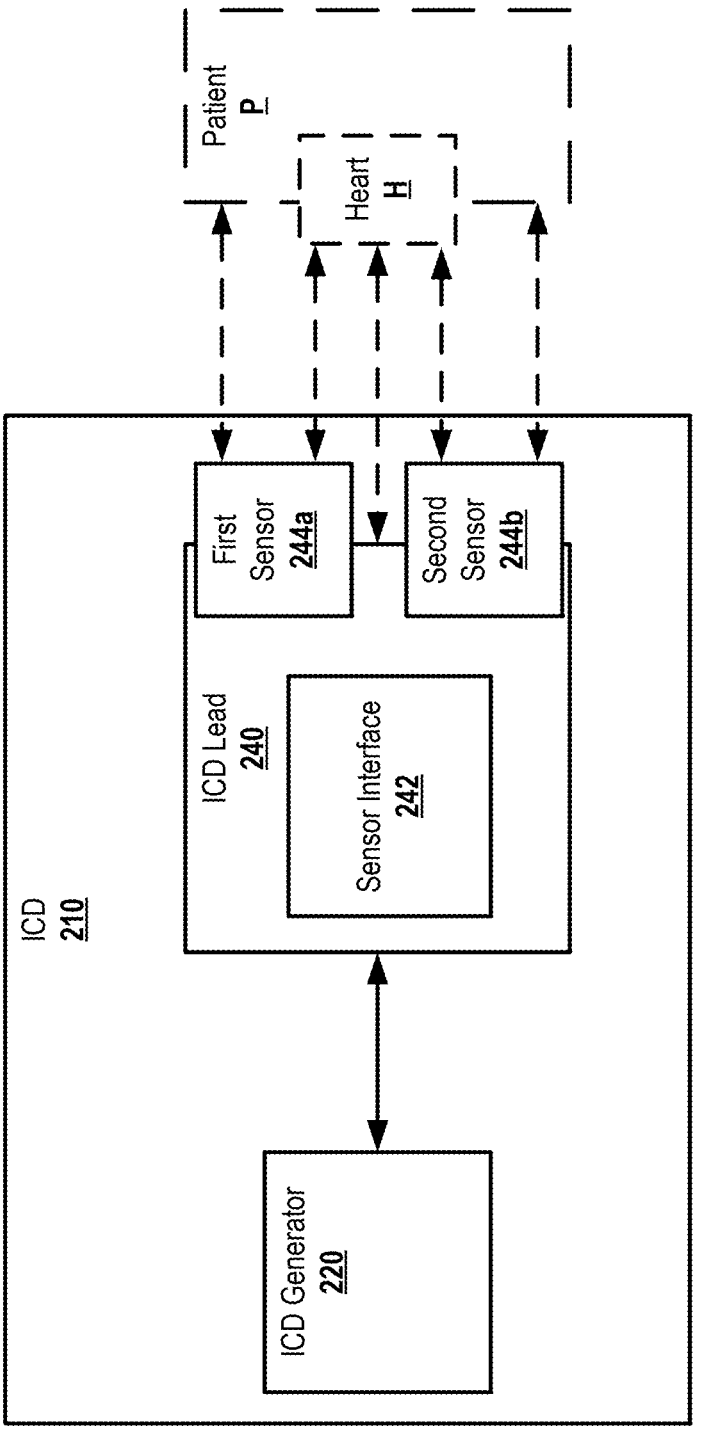
FIG. 2 schematically depicts an ICD engaging with a patient according to another embodiment.

FIG. 2 schematically depicts an ICD system 200 engaging with a patient P according to another embodiment. The ICD system 200 is structurally and/or functionally similar to the ICD system 100 of FIG. 1. The ICD system 200 includes an ICD 210 (e.g., functionally and/or structurally similar to the ICD 110 of FIG. 1) engaging with the heart H of the patient P. The ICD 210 includes an ICD generator 220 (e.g., structurally and/or functionally similar to the ICD generator 120 of FIG. 2) operatively coupled to an ICD lead 240 (e.g., structurally and/or functionally similar to the ICD lead 140 of FIG. 1. The ICD lead 240 includes a sensor interface 242 (e.g., structurally and/or functionally similar to the sensor interface 142 of FIG. 1).

The ICD 210 includes a first sensor 244*a* (e.g., structurally and/or functionally similar to the first sensor 144*a*) and a second sensor 244*b* (e.g., structurally and/or functionally similar to the second sensor 144*b*). In the embodiment shown in FIG. 2, the first sensor 244*a* and the second sensor 244*b* are integrated into the ICD lead 240. In some embodiments, such as depicted in FIG. 1, at least one of the first sensor 244*a* and/or the second sensor 244*b* are remote from the lead. The sensor interface 242 may be configured to physically couple the first sensor 244*a* and the second sensor 244*b* to the ICD lead 240. The sensor interface 242 may be configured to receive and send the outputs from the first sensor 244*a* and the second sensor 244*b*. In some embodiments, the sensor interface 242 may preprocess and/or synchronize the signals from the first sensor 244*a* and the second sensor 244*b*.

In some implementations, integrating the first sensor 244*a* and the second sensor 244*b* can allow for the sensors 244*a* and/or 244*b* to be positioned close to the heart H of the patient P. The first sensor 244*a* may be positioned along the ICD lead 240 such that cardiac signals can be measured. The second sensor 244*b* may be positioned along the ICD lead

240 such that hemodynamic status or output can be measured. In some embodiments, the first sensor 244*a* and/or the second sensor 244*b* are positioned along a region, portion, or section of the ICD lead 240. For example, the first sensor 244*a* and/or the second sensor 244*b* may be positioned along a distal section corresponding to a portion of the ICD lead 240 nearest or proximate (e.g., within 1%, within 2%, within 3%, within 4%, within 5%, within 10%, within 25%, etc.) the distal end of the ICD lead 240. In some embodiments, the first sensor 244*a* and/or the second sensor 244*b* is/are positioned at the distal end of the ICD lead 240. In some implementations, integrating the first sensor 244*a* and the second sensor 244*b* directly into the ICD lead 240 can potentially decrease the noise in the signals from the first sensor 244*a* and the second sensor 244*b* as the signal may have to travel a shorter distance and/or through fewer interfaces.

While the ICD system 200 is described above as including "the first sensor 244*a*" and "the second sensor 244*b*," it should be understood that the first sensor 244*a* can be a single sensing device or multiple sensing devices that collectively function as the first sensor 244*a*, and similarly, the second sensor 244*b* can be a single sensing device or multiple sensing devices that collectively function as the second sensor 244*b*. In some implementations, multiple sensing devices can allow for sensor data that includes multiple signal vectors (e.g., multiple cardiac electrical and/or mechanical signal vectors). Similarly, while the ICD system 200 is described herein as including "the first sensor 244*a*" and "the second sensor 244*b*," it should be understood that the ICD system 200 can include any number of additional sensors configured to sense and/or detect any suitable characteristic(s) associated with the patient (e.g., cardiac electrical and/or mechanical signals or any suitable non-cardiac signals). In some implementations, each sensor can be configured to sense and/or detect a different characteristic associated with the heart, or more generally, the patient. In some implementations, one or more sensors can be configured to sense or detect the same characteristic, thereby allowing for confirmation/verification of signal data and/or a desired degree of sensitivity and/or specificity in interpreting the signal data.

Figure 3:
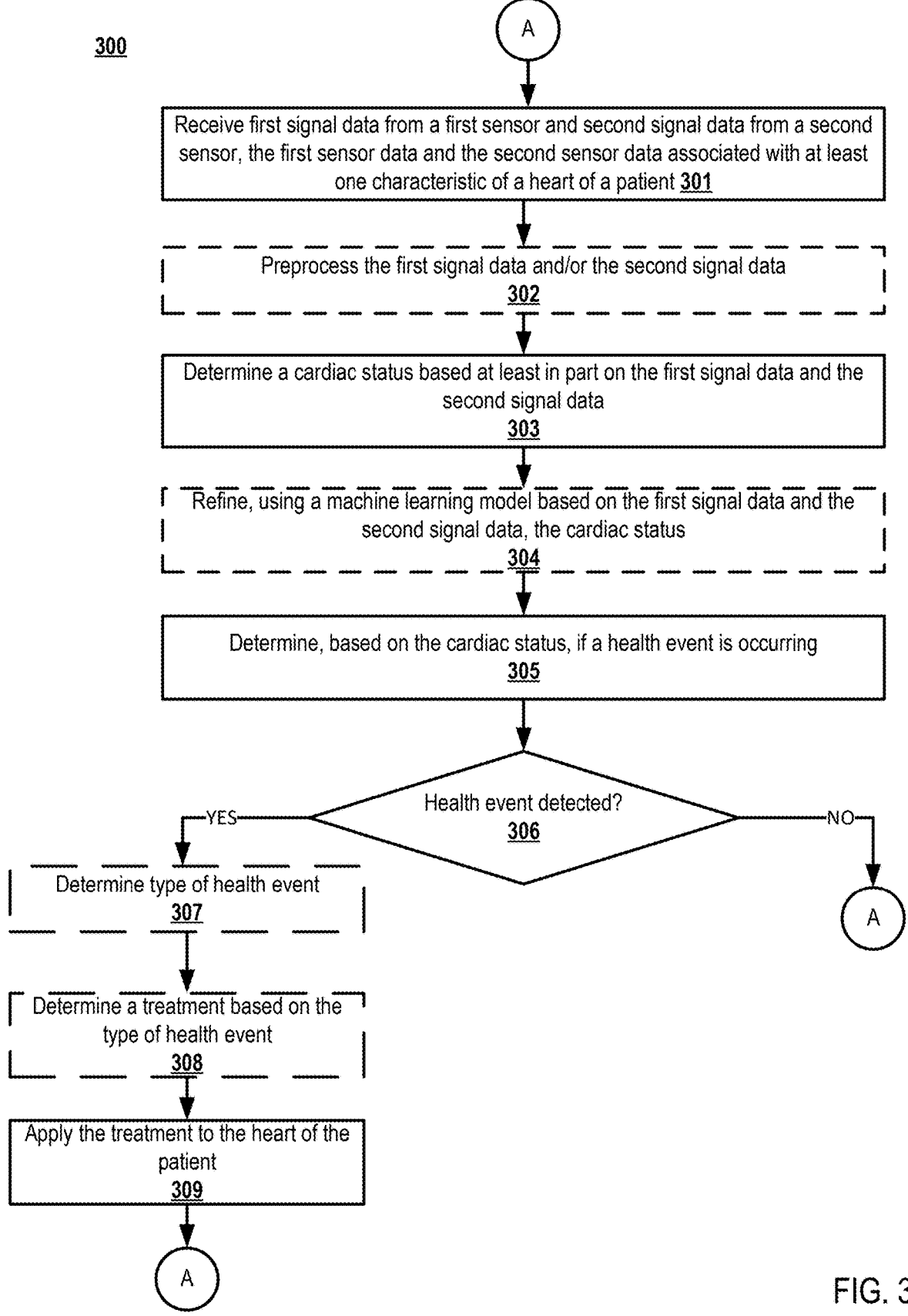
FIG. 3 is a flow chart depicting a method for determining if a patient is having a health event and whether to apply a corresponding corrective action according to an embodiment.

FIG. 3 is a flow chart depicting a method 300 for determining if a patient is having a health event and whether to apply a corresponding corrective action according to an embodiment. In some embodiments, the method 300 can be executed and/or performed by an ICD system that is functionally and/or structurally similar to the ICD system 100 of FIG. 1 and/or the ICD system 200 of FIG. 2. In some embodiments, the method 300 can be executed by one or more devices. For example, the method 300 can be executed by the ICD system 500 of FIG. 5. The method 300 is configured to use data associated with at least two characteristics of the heart or a function of the heart. In some implementations, the method 300 is configured to use at least two signals from at least two data sources (e.g., sensors) to determine if a patient is having a health event (e.g., cardiac arrest, tachycardia, arrhythmias). Using at least two signals reduces the likelihood that the ICD system determines a health event is occurring when compared to an ICD system that uses only one signal for determining if a health event is occurring. Additionally, the method 300 allows for determining the type of corrective action (e.g., treatment) to be determined based on the health event determined. This allows the ICD system to more accurately treat (e.g., with greater sensitivity and specificity) the health event and reduce the likelihood of sudden cardiac arrest. The method 300 may improve sensitivity and specificity of treatment for ventricular tachycardia or ventricular fibrillation.

The method 300 includes, at 301, receiving signal data from a first sensor (e.g., functionally and/or structurally similar to the first sensor 144a of FIG. 1 and/or the first sensor 244a of FIG. 2) and second signal data from a second sensor (e.g., structurally and/or functionally similar to the second sensor 144b of FIG. 1 and/or the second sensor 244b of FIG. 2). The first signal data and the second signal data are associated with at least one characteristic of a heart of a patient. In some embodiments, the first sensor is a sensor configured to measure or sense cardiac electrical signals and the first signal data is associated with, for example, cardiac signals, QRS complex morphology, and/or the like. In some embodiments, the second sensor is a sensor configured to measure cardiac mechanical signals (e.g., hemodynamic status) and the second signal data is associated with cardiac mechanical signals (e.g., hemodynamic status data or a proxy or derivative thereof) and/or output of the heart of the patient. In some embodiments, 301 may include receiving additional signal data from any number of additional sensors and/or additional data sources (e.g., one or more ex vivo data sources). In some embodiments, 301 may include receiving at least one of the first signal data and/or the second signal data from an external data source (e.g., patient database, etc.).

At 302, the method 300 optionally includes preprocessing the first signal data and/or the second signal data. Preprocessing can include noise reduction, filtering, amplification, normalization, conversion (e.g., analog-to-digital, etc.), synchronization, and/or the like. Preprocessing can prepare for the signals to be received by another component of the ICD system. For example, a sensor interface (e.g., functionally and/or structurally similar to the sensor interface 142 of FIG. 1 and/or the sensor interface 242 of FIG. 2) can preprocess the first signal data and the second signal data so that the first signal data and the second signal data can be received by an ICD generator (e.g., structurally and/or functionally similar to the ICD generator 120 of FIG. 1 and/or the ICD generator 220 of FIG. 2) and/or a compute device (e.g., functionally and/or structurally similar to the compute device 550 of FIG. 5). In some embodiments, the compute device and/or the ICD generator may preprocess the first signal data and/or the second signal data to prepare the data for processing.

At 303, the method 300 includes determining a cardiac status based at least in part on the first signal data and the second data signal. The cardiac status can correspond to the status of the heart (e.g., heartbeat profile, cardiac activity, etc.). In some embodiments, determining a cardiac status can further be based on data from additional source (e.g., additional sensors and/or one more ex vivo data sources). Determining cardiac status can include, for example, comparing and synchronizing the signal data and artifacts in the signal data to determine the cardiac status or functioning of the heart. For example, when the first signal data is associated with cardiac electrical signals (e.g., cardiac signals or used to determine cardiac rate) and the second signal data is associated with hemodynamic status and/or output, determining cardiac status can include synchronizing an electrical signal curve (from the first signal data) and a pressure curve (from the second signal data) to correlate the signal data. As another example, determining the cardiac status can include determining if a rhythm seen in the cardiac electrical signal data has an expected corresponding result in the hemodynamic status and/or output signal data. As such, using the first signal data and the second signal data provides a more sensitivity and specificity in determining cardiac status than when determining cardiac status using just one source of data (e.g., cardiac electrical signals alone).

At 304, the method 300 optionally includes refining the cardiac status using a machine learning model based on the first signal data and the second signal data. Refining can include, for example, improving, tuning, updating, and/or verifying the cardiac status determined at 303. The machine learning model can be trained based on cardiac status associated with data form the first sensor and the second sensor. For example, the machine learning model can be trained based on cardiac status associated with cardiac electrical signal data (e.g., cardia rate) and hemodynamic status and/or output data from the patient, historical data, data from studies, medical professional input, and/or the like. In some embodiments, the machine learning model can be trained based on additional patient data (e.g., activity level, height, weight, age, and/or the like). Training on patient data allows for the machine learning model to gain further insight on the patient that may affect the characteristics of the heart measured by the sensors.

In some embodiments, the cardiac status may be changed, updated, tuned, etc., based at least in part on comparing the cardiac status from 303 to more closely align with empirical data, a status determination by one or more trained cardiologists, updated clinical evidence, and/or any suitable known or accepted ground truth. In some embodiments, the machine learning model may be configured to recognize long-term changes in cardiac status and/or the first signal data and/or the second signal data and adapt to these changes. For example, the machine learning model may recognize that hemodynamic output has been decreasing over weeks, months, or years. Recognizing changes allows the machine learning model to adapt the ICD treatment along with the patient as the patient changes. In some embodiments, the machine learning model may receive feedback data and/or training sets that are used to further train the machine learning model.

At 305, the method 300 includes determining, based on the cardiac status, if a health event is occurring. Determining if a health event is occurring can include, in some embodiments, comparing the cardiac status to an expected cardiac status. For example, if the cardiac status indicates that a heartbeat is higher than it expected, the presence of a health event may be determined. In some embodiments, a machine learning model can be used to determine if a health event is present based at least in part on the cardiac status. For example, the machine learning model can recognize changes in the patient's heart activity that can indicate the presence of a health event, or if no health event is occurring. In some embodiments, an indication that a health event is occurring may be sent to the user. In some embodiments, the machine learning model can recognize when the patient's heart activity is expected and/or predicted to increase. For example, when the patient is exercising, experiencing stress or anxiety, and/or the like.

At 306, the method 300 includes a decision of whether a health event has been detected. If a health event has not been detected, the method 300 returns to 301 to continue monitoring the heart of the patient. If a health event has been detected, the method 300 continues to 307.

At 307, the method 300 optionally includes determining a type of health event. In some embodiments, determining a type of health event can include comparing and matching the cardiac status to known health events. In some embodiments, a machine learning model may be used to match the cardiac status to a health event. In some embodiments, the type of health event can be sent to a user device and/or the like for review by the user. For example, the type of health event can be reviewed by the patient, a medical proxy, a medical professional, and/or the like. At 308, the method 300 optionally includes determining a treatment based on the type of health event determined in 307. The treatment can correspond to the type of health event and/or can be adjusted based on information about the patient and/or the characteristics of the heart (e.g., heartrate, blood pressure, arrhythmia classification, cardiac status, hemodynamic status, etc.) at the time of or leading up to the health event. Determining the treatment based on the type of health event allows for a more accurate treatment for the given health event than when a predetermined treatment is used for any/all detected health events. For example, if, at 307, the health event is determined and/or predicted to be ventricular tachycardia, the ICD treatment may be anti-tachycardia pacing. On the other hand, if the health event is determined and/or predicted to be ventricular fibrillation, the ICD treatment may be shock therapy (e.g., defibrillation shock(s)). In some embodiments, 308 may include determining if the health event is still occurring. If the health event is determined to no longer be occurring, 308 may include determining that a treatment is not desired. Said another way, step 308 can include delaying potential treatment to confirm that the health event is still occurring, which in some instances, may reduce what may otherwise be an "appropriate" shock therapy.

At 309, the method 300 includes applying the treatment to the heart of the patient. The treatment, either predetermined or as determined in 308, is generated by the ICD generator and delivered to the heart via the ICD lead. After the treatment is delivered to the heart, the method 300 return to 301 to continue monitoring the cardiac activity of the heart of the patient. The method 300 repeats as long as the ICD is powered and/or the ICD is implanted in the patient.

While the method 300 is described above as receiving first signal data from the first sensor and second signal data from the second sensor, it should be understood that the first sensor can be a single sensing device or multiple sensing devices that collectively function as the first sensor, and similarly, the second sensor can be a single sensing device or multiple sensing devices that collectively function as the second sensor. In some implementations, multiple sensing devices can allow for sensor data that includes multiple signal vectors (e.g., multiple cardiac electrical and/or mechanical signal vectors).

In some implementations, the method 300 may optionally include receiving signal data from one or more additional sensors (e.g., in addition to the first sensor and the second sensor). In some implementations, each sensor can be configured to sense and/or detect a different characteristic associated with the heart, or more generally, the patient. In some implementations, one or more sensors can be configured to sense or detect the same characteristic, thereby allowing for confirmation/verification of signal data and/or a desired degree of sensitivity and/or specificity in interpreting the signal data. For example, in some implementations, the step at 301 can include receiving signal data from any number of sensors or data sources included in or in communication with the ICD; the optional step at 302 may include preprocessing the signal data from each of the sensors; the step at 303 may include determining the cardiac status based at least in part on each or all of the signal data; and the optional step at 304 may include refining the cardiac status using a machine learning model based on each or all of the signal data.

Figure 4:
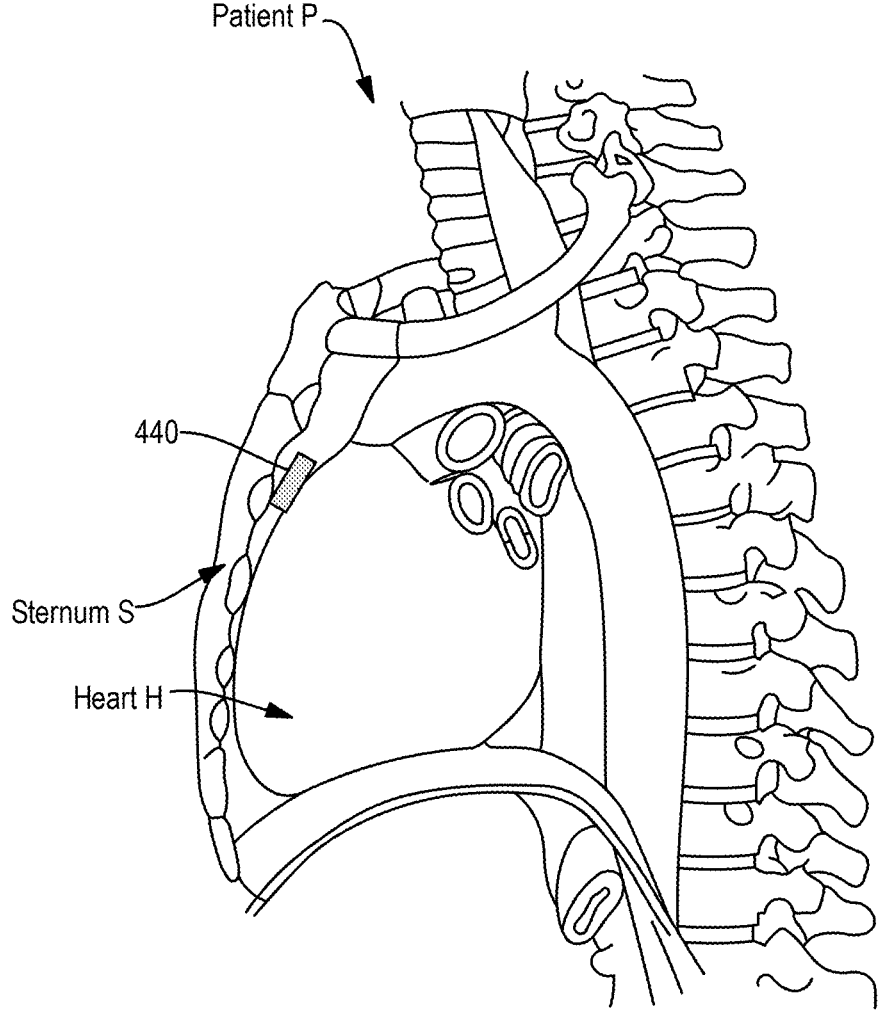
FIG. 4 depicts a placement of an ICD lead in the chest of a patient according to an embodiment.

FIG. 4 depicts a placement of an ICD lead 440 in the chest of a patient according to an embodiment. In some embodiments, the ICD lead 440 is structurally and/or functionally similar the ICD lead 140 of FIG. 1 and/or the ICD lead 240 of FIG. 2. The ICD lead 440 is coupled to an ICD generator (e.g., structurally and/or functionally similar to the ICD generator 120 of FIG. 1 and/or the ICD generator 220 of FIG. 2) to form an ICD (e.g., structurally and/or functionally similar to the ICD 110 of FIG. 1 and/or the ICD 210 of FIG. 2). The position of the ICD lead 440 can be a parameter and/or factor in reducing anti-tachycardia pacing (ATP) thresholds. ATP thresholds that are higher than desired could result in inconsistent pacing, intolerable sensations to the patient during pacing, or non-use of pacing that increases probability of undesirable health events and/or undesirable shocks.

As seen in FIG. 4, the ICD lead 440 is positioned in the substernal space between a sternum S and a pericardium of a heart H of a patient P. The ICD lead 440 is positioned in the substernal space since any space between the electrode and the pericardium can increase pacing thresholds. Furthermore, the ICD lead 440 is configured to facilitate the natural movement of the heart H that occurs with each cardiac cycle. In some embodiments, the ICD lead 440 can facilitate natural movement by using the sternum S as a base and having the ICD lead 440 pressed against or otherwise placed in contact with the fibrous layer of the pericardium. This position allows for the ICD lead 440 to move in multiple directions and absorb and/or move with the motion of the heart H.

Figure 5:
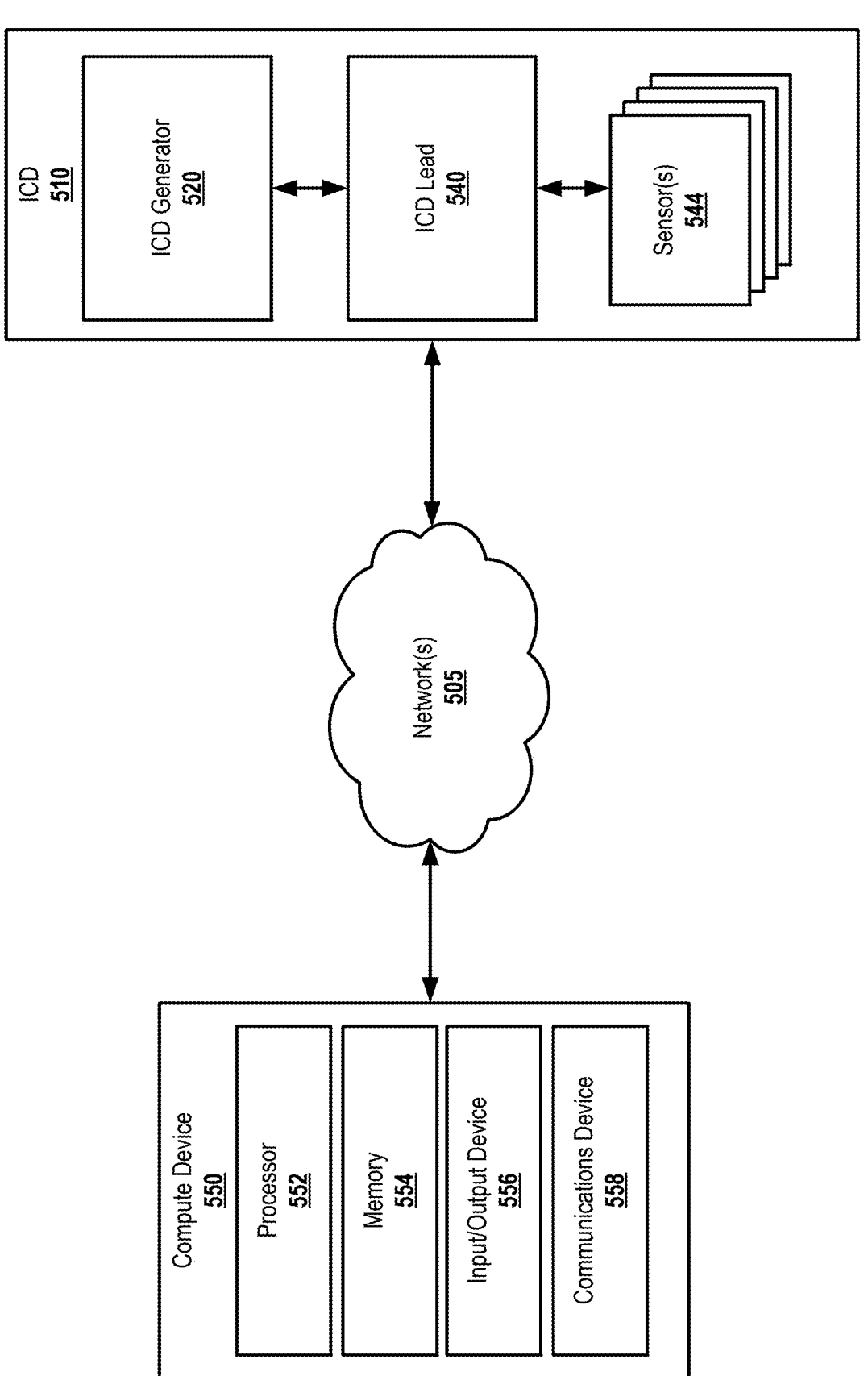
FIG. 5 depicts an ICD in communication with an external compute device via a network according to an embodiment.

FIG. 5 depicts an ICD 510 (e.g., functionally and/or structurally similar to the ICD 110 of FIG. 1 and/or the ICD 210 of FIG. 2) in communication with an external compute device 550 via network(s) 505 according to an embodiment. The network(s) 505 can include one or more network(s) that may be any type of network (e.g., a local area network (LAN), a wide area network (WAN), a virtual network, a telecommunications network) implemented as a wired network and/or wireless network (e.g., Wi-Fi, Bluetooth®, Bluetooth® low energy, Zigbee, etc.) and used to operatively couple to any compute device, including, for example, the compute device 550 and/or the ICD 510. In some embodiments, the components of the ICD 510 can be configured to communicate directly with the network(s) 505. For example, the ICD generator 520 (e.g., structurally and/or functionally similar to the ICD generator 120 of FIG. 1 and/or the ICD generator 220 of FIG. 2) may send and receive information associated with cardiac status, health events, and/or treatment to the compute device 550 (or any other suitable device) via the network(s) 505. As another example, the ICD lead 540 (e.g., structurally and/or functionally similar to the ICD lead 140 of FIG. 1 and/or the ICD lead 240 of FIG. 2) may send and/or receive processed signal data to compute device 550 (or any other suitable device) via the network(s) 505. As another example, the sensor(s) 544 (e.g., structurally and/or functionally similar to the first sensor 144a of FIG. 1, the second sensor 144b of FIG. 1, the first sensor 244a of FIG. 1, and/or the second sensor 244b of FIG. 2) can send and receive information associated with the signals and/or the operation of the sensor(s) 544.

The compute device 550 is an external device configured to receive and send signals, data, and/or information from/to the ICD 510 via the network(s) 505. The compute device 550 may be any suitable device or combination of devices. For example, the compute device 550 can be any suitable electronic device configured to send, receive, process, analyze, store, use, change, define, etc. data, data structures, and/or the like. The components of the compute device(s) can be contained within a single housing or machine or can be distributed within and/or between multiple physical machines, virtual machines, and/or any combination thereof. In some embodiments, the compute device(s) 550 can be physically included in and/or on local machine(s) or device (s) or can be stored, run, executed, and/or otherwise implemented in and/or on remote machine(s) or device(s). For example, the compute device 550 (or a portion or component thereof) can be and/or can include, but is not limited to, personal computer(s) (PC), laptop PC(s), tablet PC(s), mobile device(s) (e.g., a smart phone, wearable, etc.), server device(s), workstation(s), and/or the like. In some embodiments, the compute device 550 or at least a portion thereof can be implemented as a virtual machine and/or virtual private server executed on and/or run as an instance or guest on a physical machine and/or cloud platform like Microsoft Azure®, Amazon® web services, IBM® cloud computing, etc.

The compute device 550 includes a processor 552 a memory 554, an input/output (I/O) device 556, and a communication device 558. The processor 552 can be and/or can include one or more data processors, image processors, graphics processing units (GPU), digital signal processors (DSP), analog signal processors, mixed-signal processors, machine learning processors, deep learning processors, finite state machines (FSM), compression processors (e.g., data compression to reduce data rate, bandwidth, and/or memory requirements), encryption processors (e.g., for secure wireless data and/or power transfer), and/or the like. The processor 552 can be, for example, a general-purpose processor, central processing unit (CPU), microprocessor, microcontroller, Field Programmable Gate Array (FPGA), an Application Specific Integrated Circuit (ASIC), a processor board, a virtual processor, and/or the like. The underlying device technologies may be provided in a variety of component types such as metal-oxide semiconductor field-effect transistor (MOSFET) technologies like complementary metal-oxide semiconductor (CMOS), bipolar technologies like generative adversarial network (GAN), polymer technologies (e.g., silicon-conjugated polymer and metal-conjugated polymer-metal structures), mixed analog and digital technologies, and/or the like.

The memory 554 can be, for example, a random-access memory (RAM), static RAM (SRAM), dynamic RAM (DRAM), a synchronous dynamic RAM (SDRAM), a memory buffer, a read-only memory (ROM), an erasable programmable read-only memory (EPROM), an electrically erasable read-only memory (EEPROM), flash memory, volatile memory, non-volatile memory, combination(s) thereof, types or subtypes or variations thereof, and/or the like. In some embodiments, the memory 554 can store instructions to cause the processor to execute modules, processes, and/or functions associated with the compute device, such as sending/receiving data, aggregating data, analyzing data, executing any number of models or algorithms (e.g., machine learning models, etc.), controlling any number of controllers, machines, devices, and/or components.

The input/output (I/O) device 556 can be and/or can include any suitable device(s), interface(s), port(s), etc. that can allow the compute device 550 to receive an input and/or to provide an output. For example, in some implementations, an input can include a port or wireless communication device configured to communicate with and/or receive input from a keyboard, mouse, and/or any other peripheral device.

In some implementations, an output can include a port or wireless communication device configured to communicate with and/or provide output to an audio device, a display device, a haptic device, and/or any other suitable device. For example, an I/O device 556 can be, can include, and/or can be configured to at least partially control a display that can provide at least a portion of a user interface for a software application (e.g., a mobile application, a PC application, an internet web browser, etc.) installed and/or executed on or by the compute device (or the processor thereof). In such implementations, the display can be, for example, a cathode ray tube (CRT) monitor, a liquid crystal display (LCD) monitor, a light emitting diode (LED) monitor, and/or the like.

The communication device 558 can be any suitable device (s) and/or interface(s) that can communicate with and/or via the network(s) 505. The communication device 558 can include one or more wired and/or wireless interfaces, such as, for example, Ethernet interfaces, optical carrier (OC) interfaces, and/or asynchronous transfer mode (ATM) interfaces. In some embodiments, the communication device 558 can be, for example, a network interface card and/or the like that can include at least an Ethernet port and/or a wireless radio (e.g., a Wi-Fi® radio, a Bluetooth® radio, near field communications (NFC) radio, etc.). In some embodiments, the communication device 558 can be configured to receive/ send signals and/or data from/to any number of devices, data sources, assets, machines, controllers, sensors, systems, etc. via the network. Moreover, the communication device 558 is in communication with the processor 552, the memory 554, and the I/O device 556 allowing signals and/or data to be transmitted therebetween.

In some embodiments, the compute device 550 may be configured to execute any of the processes and/or any suitable portion of the processes described in reference to the ICDs described herein, such as the ICD 110 of FIG. 1 and/or the ICD 210 of FIG. 2. For example, the compute device 550 may be configured to store instructions for and/or execute instructions related to using machine learning models and/or algorithms. The compute device 550 can be configured to complete computations that may be too resource (e.g., battery power, memory, processing power, etc.) for the ICD 510.

For example, the compute device 550 may be configured to execute, via the processor 552, machine learning model processes for the ICD 510. In some embodiments, the compute device 550 may be configured to receive signals and/or data associated with the sensor(s) 544, determine a cardiac status and a health event occurring, and/or determine a treatment for the health event. In some embodiments, the compute device 550 may be configured to send commands and/or outputs to the ICD 510 so that the ICD 510 can, in turn, deliver treatment to the heart of the patient. In some embodiments, the compute device 550 may be configured to send commands and/or outputs to the ICD 510 that can cause the ICD 510 to update firmware, data stored in one or more repositories (e.g., databases), and/or instructions stored in the memory 554. As such, the ICD 510 can adapt to treatment decisions based on patient changes over time.

The input/output device 556 of the compute device can include a device to input signals and/or commands into the compute device 550 and/or output signals and/or commands. For example, the input/output device 556 can include a device (e.g., touchscreen, keyboard, mouse, etc.) for inputting inputs by a user (e.g., doctor, patient, caretaker, etc.) to input information associated with the patient and regarding the operation of the ICD 510. In some embodiments, a user may input training sets for a machine learning model. The I/O device 556 may include a device (e.g., screen, light, etc.) configured to output information regarding the ICD 510. For example, the I/O device 556 can display the status (e.g., battery status, operational status, etc.) of the ICD 510, information associated with health events, information associated with treatment, and/or the like.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; solid state storage media such as a solid state drive (SSD) and/or a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, an FPGA, an ASIC, and/or the like. Software modules (executed on hardware) can be expressed in a variety of software languages (e.g., computer code), including C, C++, Java™, Ruby, Visual Basic™, Python™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools, and/or combinations thereof (e.g., Python™). Additional examples of computer code include, but are not limited to, control signals, encrypted code, and compressed code.

While various schematics, embodiments, and/or implementations have been described above, it should be understood that they have been presented by way of example only, and not limitation. Various modifications, changes, and/or variations in form and/or detail may be made without departing from the scope of the disclosure and/or without altering the function and/or advantages thereof unless expressly stated otherwise. Likewise, while embodiments and/or features, components, configurations, aspects, etc. thereof may be described above in the context of certain implementations, it should be understood that such implementations are presented by way of example only and not limitation. Any of the embodiments and/or features, components, configurations, aspects, etc. thereof can be used in, and/or adapted for use in, other implementations unless expressly stated otherwise. Functionally equivalent embodiments, implementations, and/or methods, in addition to those described herein, will be apparent to those skilled in the art from the foregoing descriptions and are intended to fall within the scope of the disclosure.

Where schematics, embodiments, and/or implementations described above indicate certain components arranged in certain orientations, configurations, or positions, the arrangement of components may be modified. Although various embodiments have been described as having particular features, configurations, and/or combinations of components, other embodiments are possible having a combination of any features, configurations, and/or components from any of embodiments described herein, except mutually exclusive combinations. The embodiments described herein can include various combinations and/or sub-combinations of the functions, components, configurations, and/or features of the different embodiments described.

The specific configurations of the various components can also be varied. For example, the size and specific shape of the various components can be different from the embodiments shown, while still providing the functions as described herein. More specifically, the size and shape of the various components can be specifically selected for a desired or intended usage. Thus, it should be understood that the size, shape, and/or arrangement of the embodiments and/or components thereof can be adapted for a given use unless the context explicitly states otherwise.

Where methods described above indicate certain events occurring in certain order, the ordering of certain events may be modified. Additionally, certain of the events may be performed concurrently in a parallel process, when possible, as well as performed sequentially as described above. While methods have been described as having particular steps and/or combinations of steps, other methods are possible having a combination of any steps from any of methods described herein, except mutually exclusive combinations and/or unless the context clearly states otherwise.

What is claimed is:

1. A method for improving treatment decisions of an implantable cardioverter defibrillator (ICD) implanted in a patient, the method comprising:

determining an electrical status of a heart of the patient based on a first signal received from an electrical sensor of an ICD lead that is implanted in an anterior mediastinum of the patient, the electrical sensor configured to detect electrical signals radiating from the heart;

calculating a hemodynamic output of the heart based on a second signal received from a pressure sensor of the ICD lead, the pressure sensor configured to detect pressure changes in the anterior mediastinum due to a mechanical functioning of the heart; and defining, based on a correlation between the electrical status and the hemodynamic output of the heart, a treatment decision associated with delivering a shock treatment to the heart.

2. The method of claim 1, wherein the defining of the treatment decision includes defining a decision to deliver the shock treatment to the heart when a degree of correlation between the electrical status and the hemodynamic output is above a threshold degree of correlation.

3. The method of claim 2, further comprising:

delivering shock treatment in response to the degree of correlation between the electrical status and the hemodynamic output being above the threshold degree of correlation.

4. The method of claim 3, wherein the delivering of the shock treatment includes delivering, via a treatment element of the ICD lead, high-power treatment energy to the heart of the patient.

5. The method of claim 1, wherein the defining of the treatment decision includes defining a decision to deliver a first treatment when a degree of correlation between the electrical status and the hemodynamic output is above a threshold degree of correlation and to deliver a second treatment different from the first treatment when the degree of correlation between the electrical status and the hemodynamic output is below a threshold degree of correlation.

6. The method of claim 5, wherein the first treatment includes delivering a defibrillation shock to the heart of the patient and the second treatment includes delivering cardiac pacing to the heart of the patient.

7. The method of claim 6, wherein the delivering of the cardiac pacing includes delivering, via a treatment element of the ICD lead, low-power treatment energy to the heart of the patient.

8. The method of claim 1, wherein the defining of the treatment decision includes defining a decision to deliver the shock treatment when a degree of correlation between the electrical status and the hemodynamic output is above a threshold degree of correlation and to not deliver the shock treatment when the degree of correlation between the electrical status and the hemodynamic output is below the threshold degree of correlation.

9. A non-transitory processor-readable medium storing code representing instructions to be executed by a processor, the code comprising code to cause the processor to:

determine an electrical status of a heart of a patient based on a first signal received from an electrical sensor of an ICD lead that has been implanted in an anterior mediastinum of a patient, the electrical sensor configured to detect electrical signals radiating from the heart;

calculate a hemodynamic output of the heart based on a second signal received from a pressure sensor of the ICD lead, the pressure sensor configured to detect pressure changes in the anterior mediastinum due to a mechanical functioning of the heart; and define, based on a correlation between the electrical status and the hemodynamic output of the heart, a treatment decision associated with delivering a shock treatment to the heart.

10. The non-transitory processor-readable medium of claim 9, wherein the code that causes the processor to define the treatment decision further includes code to cause the processor to define a decision to deliver the shock treatment when a degree of correlation between the electrical status and the hemodynamic output is above a threshold degree of correlation.

11. The non-transitory processor-readable medium of claim 10, the code further comprising code to cause the processor to:

send, to a generator of the ICD, an instruction to generate the shock treatment in response to the degree of correlation between the electrical status and the hemodynamic output being above the threshold degree of correlation.

12. The non-transitory processor-readable medium of claim 10, wherein the shock treatment includes high-power treatment energy, the ICD lead including a treatment element configured to deliver the high-power treatment energy to the heart of the patient.

13. The non-transitory processor-readable medium of claim 9, wherein the code that causes the processor to define the treatment decision further includes code to cause the processor to send, to a generator of the ICD, an instruction to generate a first shock treatment energy when a degree of correlation between the electrical status and the hemodynamic output is above a threshold degree of correlation and to generate a second shock treatment energy different from the first shock treatment when the degree of correlation between the electrical status and the hemodynamic output is below a threshold degree of correlation.

14. The non-transitory processor-readable medium of claim 13, wherein the first shock treatment energy is a defibrillation shock energy, and the second shock treatment energy is a cardiac pacing energy.

15. The non-transitory processor-readable medium of claim 14, wherein the defibrillation shock energy is a high-power treatment energy, and the cardiac pacing energy is a low-power treatment energy.

16. The non-transitory processor-readable medium of claim 9, wherein the code that causes the processor to define the treatment decision further includes code to cause the processor to send, to a generator of the ICD, an instruction to generate the shock treatment when a degree of correlation between the electrical status and the hemodynamic output is above a threshold degree of correlation and to not generate the shock treatment when the degree of correlation between the electrical status and the hemodynamic output is below the threshold degree of correlation.

17. A system, comprising:

an electrical sensor coupled to a lead configured to be implanted in an anterior mediastinum of a patient, the electrical sensor configured to detect electrical signals radiating from a heart of the patient;

a pressure sensor coupled to the lead, the pressure sensor configured to detect pressure changes in the anterior mediastinum due to a mechanical functioning of the heart; and an implantable cardioverter defibrillator (ICD) configured to be implanted in the patient, the ICD including a generator coupled to the lead when the lead is implanted in the anterior mediastinum, the generator including a memory and a processor configured to execute instructions stored in the memory operable to cause the processor to:

determine an electrical status based on a first signal received from the electrical sensor;

calculate a hemodynamic output of the heart based on a second signal received from the pressure sensor; and define, based on a correlation between the electrical status and the hemodynamic output of the heart a treatment decision associated with delivering a shock treatment to the heart.

18. The system of claim 17, wherein the treatment decision includes a decision to operate the generator to deliver, to the heart of the patient via a treatment element of the lead, the shock treatment to the heart when a degree of correlation between the electrical status and the hemodynamic output is above a threshold degree of correlation.

19. The system of claim 18, wherein the treatment decision includes a decision to withhold the shock treatment when the degree of correlation between the electrical status and the hemodynamic output is below the threshold degree of correlation.

20. The system of claim 17, wherein the treatment decision includes a decision to operate the generator to deliver, to the heart of the patient via a treatment element of the lead, a defibrillation shock energy when a degree of correlation between the electrical status and the hemodynamic output is above a threshold degree of correlation and a cardiac pacing energy when the degree of correlation between the electrical status and the hemodynamic output is below a threshold degree of correlation.

21. The system of claim 17, further comprising:
an external compute device in communication with the ICD via a network, the external compute device configured to:
receive data associated with cardiac electrical signals and anterior mediastinal pressure signals,
train, using at least one of the cardiac electrical signals or the anterior mediastinal pressure signals, a machine learning model configured to predict at least one of the electrical status, the hemodynamic output, or the correlation between the electrical status and the hemodynamic output, and
send, to the ICD, a signal to cause the ICD to store in the memory an updated model that, when executed by the processor, outputs at least one of the electrical status of the heart, the hemodynamic output of the heart, or the correlation between the electrical status and the hemodynamic output of the heart.

22. The system of claim 21, wherein the updated model is configured to output the electrical status of the heart based at least in part on determining a pattern corresponding to at least one of a cardiac rate, a cardiac status, or a QRS complex.

23. The system of claim 21, wherein the external compute device is further configured to:
receive, from the ICD, data associated with the electrical signals detected by the electrical sensor and data associated with the pressure changes in the anterior mediastinum detected by the pressure sensor, and
define at least one of a long-term correlation between the electrical status of the heart of the patient and the hemodynamic output of the heart of the patient, or changes in correlation.

24. A method for improving treatment decisions of an implantable cardioverter defibrillator (ICD) implanted in a patient, comprising:

determining an electrical status based on a first signal received from an electrical sensor of an ICD lead implanted in an anterior mediastinum of a patient, the electrical sensor configured to detect electrical signals radiating from a heart of the patient;
determining a hemodynamic output of the heart based on a second signal received from a pressure sensor coupled to the ICD lead, the pressure sensor configured to detect pressure changes in the anterior mediastinum due to a mechanical functioning of the heart; and
responsive to each of the electrical status and the hemodynamic output being associated with a cardiac arrhythmia, causing a generator of the ICD to generate a shock treatment energy to be delivered via the ICD lead to the heart of the patient.

25. The method of claim 24, wherein the shock treatment energy is defibrillation shock energy.

26. The method of claim 24, wherein the shock treatment energy is defibrillation shock energy, the method further comprising:
responsive to the cardiac electrical status being associated with the cardiac arrhythmia and the hemodynamic output not being associated with the cardiac arrhythmia, causing the generator of the ICD to generate cardiac pacing energy to be delivered via the ICD lead to the heart of the patient.

27. The method of claim 26, wherein the defibrillation shock energy is a high-power treatment energy, and the cardiac pacing energy is a low-power treatment energy.

28. The method of claim 24, wherein the treatment energy is anti-tachycardia pacing energy when each of the cardiac electrical status and the hemodynamic output is associated with ventricular tachycardia.

29. The method of claim 24, wherein the shock treatment energy is defibrillation shock energy, the method further comprising:
withholding the shock treatment energy in response to the cardiac electrical status being associated with the cardiac arrhythmia and the hemodynamic output not being associated with the cardiac arrhythmia.

30. The method of claim 24, wherein the causing the generator of the ICD to generate the shock treatment energy includes causing the generator to generate the shock treatment energy when a degree of a correlation between the electrical status and the hemodynamic output is above a threshold degree of correlation.

* * * * *